United States Patent
Patel et al.

(10) Patent No.: US 9,811,637 B2
(45) Date of Patent: Nov. 7, 2017

(54) MEDICAL PILL DISPENSING SYSTEM

(71) Applicant: Meditab Software Inc., Oakland, CA (US)

(72) Inventors: Miteshkumar Ishwarbhai Patel, San Leandro, CA (US); Feros Khan Seyed Yousuf Khan, Sacramento, CA (US); Sergey Shkapov, Belmont, CA (US)

(73) Assignee: MEDITAB SOFTWARE INC., Sacramento, CA (US)

( * ) Notice: Subject to any disclaimer, the term of this patent is extended or adjusted under 35 U.S.C. 154(b) by 488 days.

(21) Appl. No.: 14/155,873

(22) Filed: Jan. 15, 2014

(65) Prior Publication Data
US 2015/0066206 A1  Mar. 5, 2015

Related U.S. Application Data

(63) Continuation-in-part of application No. 14/018,245, filed on Sep. 3, 2013.

(51) Int. Cl.
G06F 19/00 (2011.01)
G07F 17/00 (2006.01)
A61J 1/03 (2006.01)

(52) U.S. Cl.
CPC ...... *G06F 19/3462* (2013.01); *G07F 17/0092* (2013.01); *A61J 1/035* (2013.01); *A61J 2205/30* (2013.01); *A61J 2205/50* (2013.01)

(58) Field of Classification Search
CPC .. G06F 19/3456; G06F 19/3462; A61J 1/035; A61J 2205/30
USPC .......................................... 700/232, 233, 235
See application file for complete search history.

(56) References Cited

U.S. PATENT DOCUMENTS

| | | | | |
|---|---|---|---|---|
| 5,014,851 | A * | 5/1991 | Wick | A61J 1/035 206/461 |
| 6,681,935 | B1 * | 1/2004 | Lewis | A61J 1/035 206/534 |
| 8,020,702 | B2 * | 9/2011 | Strub | A61J 1/035 206/531 |
| 8,055,512 | B1 * | 11/2011 | Pankow | G06Q 10/087 705/2 |
| 8,200,366 | B2 * | 6/2012 | Ali | G06F 19/3462 53/168 |
| 8,627,639 | B2 * | 1/2014 | Ali | B65B 5/103 53/473 |
| 8,914,146 | B2 * | 12/2014 | Carson | B65B 57/16 700/213 |
| 9,073,206 | B2 * | 7/2015 | Carson | B25J 9/0096 |
| 2004/0148054 | A1 * | 7/2004 | Schwartz | A61J 1/035 700/231 |

(Continued)

*Primary Examiner* — Michael K Collins
(74) *Attorney, Agent, or Firm* — Firasat Ali; Creso Legal

(57) ABSTRACT

Systems and methods are disclosed for a medical pill dispensing system. A method involves accessing a plan. The plan indicates a first pill distribution for a first period of time, and a second pill distribution for a second period of time. The method also involves receiving an input, where the input indicates a change to the plan. The input indicates at least one pill to be distributed in the first period of time. The method also involves determining whether to modify one or more of the first pill distribution or the second pill distribution. The method involves, in response to a determination that the second pill distribution is to be modified, modifying the plan to indicate a change in the second pill distribution.

20 Claims, 28 Drawing Sheets

(56) References Cited

U.S. PATENT DOCUMENTS

| | | | |
|---|---|---|---|
| 2005/0109658 A1* | 5/2005 | Bindford | A61J 7/04 206/534 |
| 2007/0185615 A1* | 8/2007 | Bossi | G06F 19/3462 700/244 |

* cited by examiner

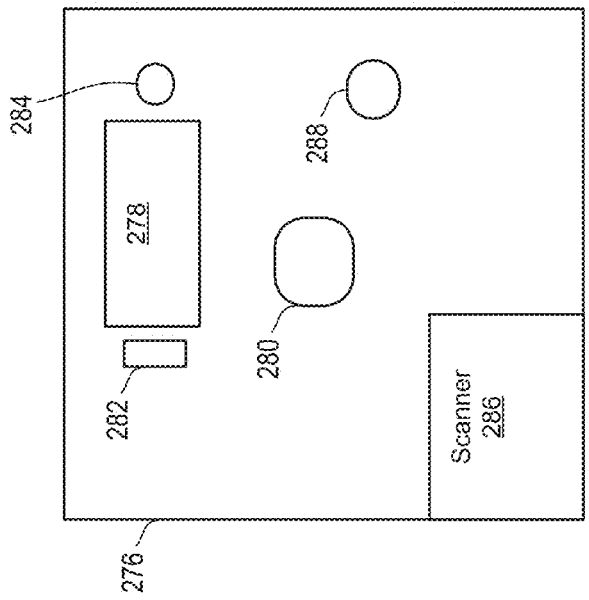
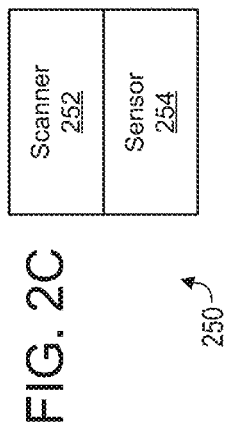
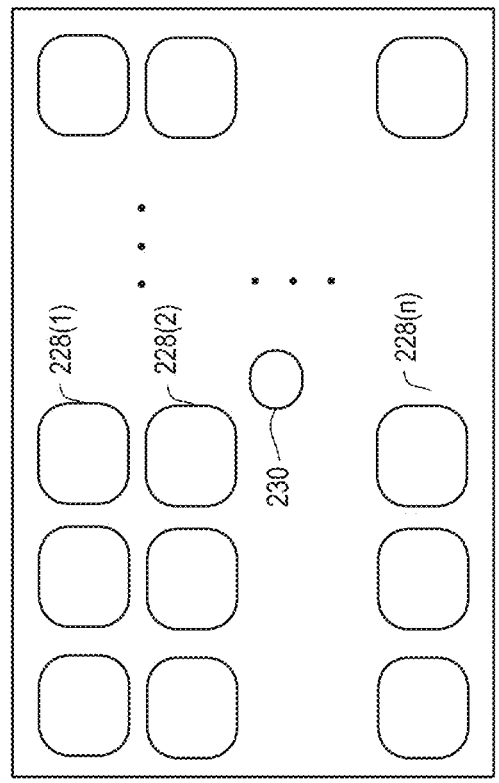

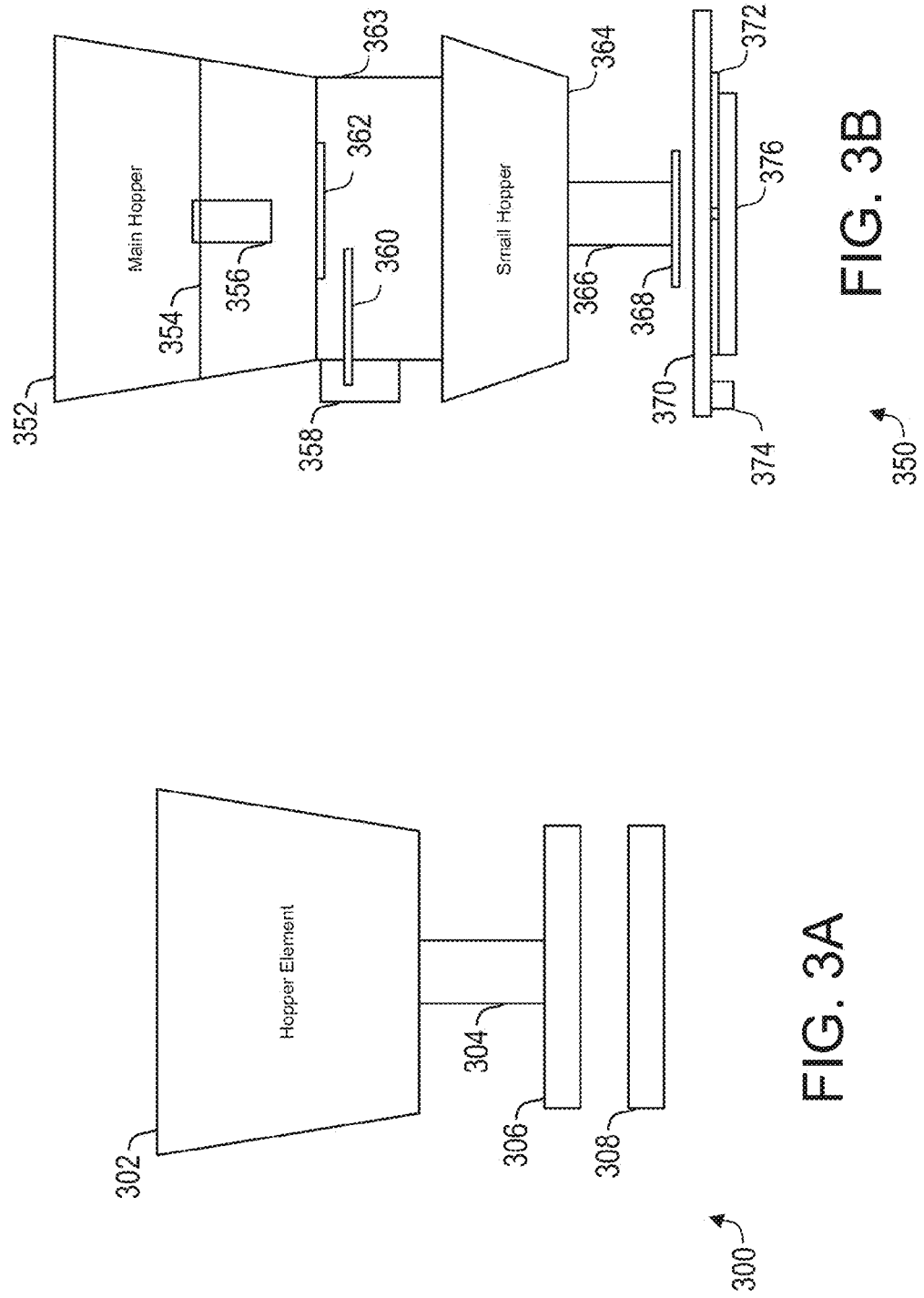

FIG. 5

MEDICAL PILL DISPENSING SYSTEM

CONTINUATION INFORMATION

This application is a continuation-in-part of an application Ser. No. 14/018,245, filed on Sep. 4, 2013, titled "MEDICATION DOSAGE DISPENSING SYSTEM AND METHODS HAVING CUSTOMIZATION AND MODIFICATION FOR MEDICINE DISPENSING CONFIGURATIONS," having Miteshkumar Ishwarbhai Patel and Hemang Vipimchandra Trivedi as inventors. Application Ser. No. 14/018,245 is also incorporated herein by reference.

BACKGROUND OF THE INVENTION

Field of the Invention

This application is related to medical pill dispensers, and more particularly, to automated medical pill dispensers.

Description of the Related Art

Medication management systems play an integral part of long-term care facilities. For example, companies recognized the need for pharmacies to provide customers a secure, affordable and fully customized solution for medication management.

Pill dispensing systems that dispense pills according to a pre-programmed schedule are widely used and are valuable in today's society. Such pill dispensers dispense different dosages of different pills at different frequencies and therefore at different times. Some pill dispensers have multiple pill chambers dispense pills contained within the chambers. However, each of these chambers contains only a single medication dose for a particular time. A single medication dose may include two, three or more different kinds of pill medications that are to be given at a particular time. Each pill chamber must then be individually filled with these different pill medications for a given particular time.

This type of pill dispensing system requires the chamber to be correctly filled with the various types and number of pill medication to be dispensed at a particular time. Thus, if a user requires medication four times a day, twenty eight chambers must be individually filled by the user for one week's worth of medication (i.e., one week's worth of pills). Additionally, the user is required to correctly count and place each pill medication into the correct pill chamber. This user intensive technique is prone to human error, makes it difficult to maintain the correct dispensing schedule and dose, and further leads to increased health costs as the result of non-compliance.

For convenience and safety, pharmacies provide the service of prepacking medications for patients using medicine trays. This process includes looking at all the medications of a patient, and determining how often a patient needs to take the medications. The medications are placed within predefined slots, such as having slots for morning and afternoon. Medications in the morning slots are taken in the morning, and so on.

A patient may take a medication dosage based on the predefined medication slots that are filled by a pharmacist in the respective trays. For example, four slots per day (morning, noon, evening and night) are configured within the tray. Furthermore, packs can be created by pharmacies that contain packages medications. Such a pack includes various medications that are taken at different times during the day. The medications can be identified graphically to help the patient visualize when to take them. A certain patient may use these multiple packs within a week, such as a different pack each day.

The medications can be placed within their respective slots of the pack so that a patient merely takes the medications in the slot at the appointed time. The patient does not need to count out medications or try to guess if the last dosage was missed. Many facilities and organizations assist patients by pre-filling the slots within medication packs.

However, even with the automated pill dispensing systems available today, many systems still rely on manual user input for both user prescriptions as well as for filling these prescriptions. In other words, the existing pill dispensing system lack one or more of reliably dispensing a correct number of various pills at predetermined times. In addition, customization of pill pack generation is virtually non-existent.

BRIEF DESCRIPTION OF THE DRAWINGS

The embodiments of the present application may be better understood, and its numerous objects, features, and advantages made apparent to those skilled in the art by referencing the accompanying drawings.

FIGS. 2A-2E are various block diagrams of canister and sensor elements of the pill dispensing robot, according to some embodiments.

FIGS. 3A and 3B are block diagrams of machine body of the pill dispensing robot, according to some embodiments.

FIG. 5 is a block diagram of a pill pack used by the pill dispensing robot, according to some embodiments.

Figure 1A:
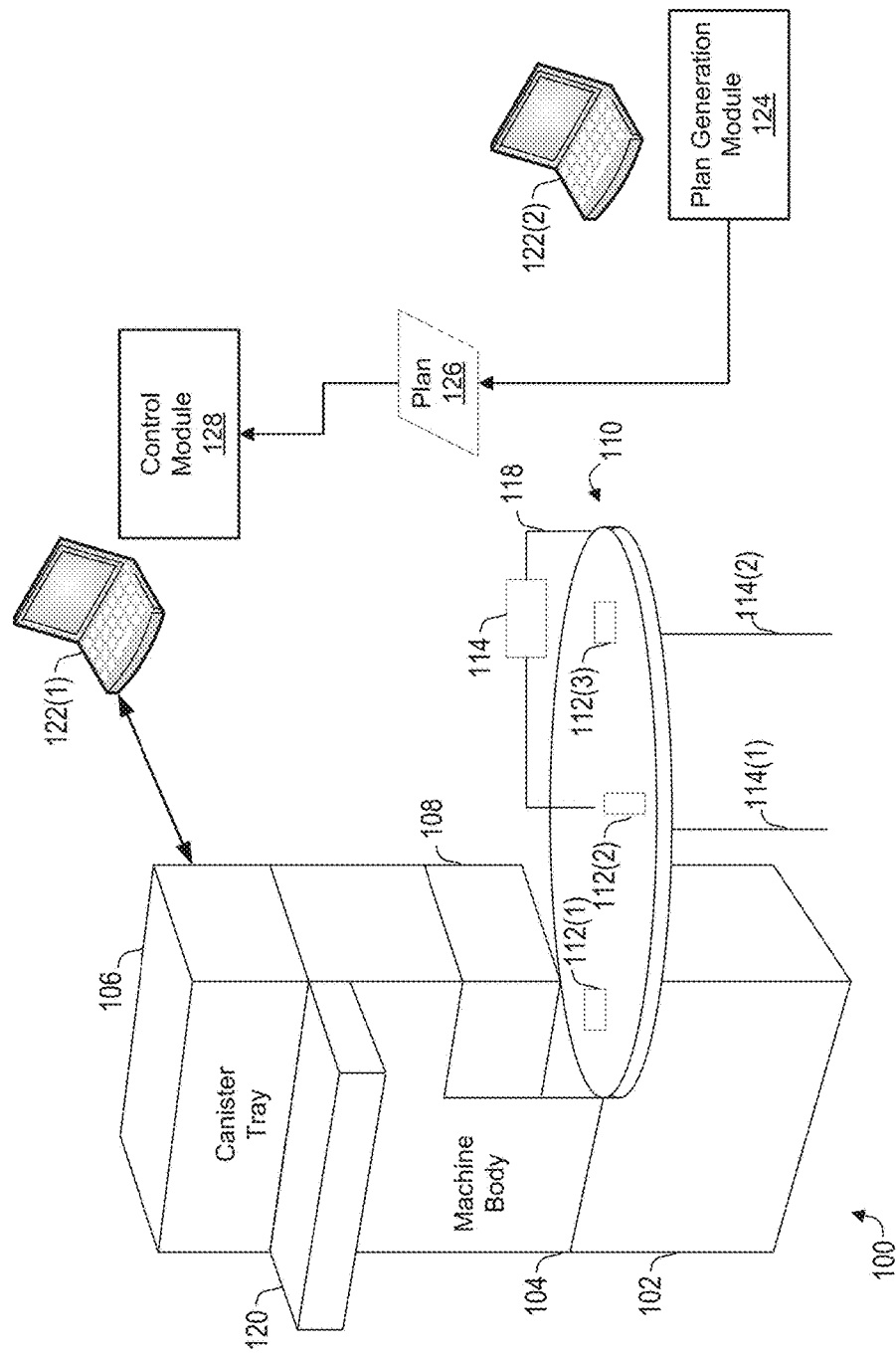
FIG. 1A is a block diagram of a general view of a pill dispensing robot, according to some embodiments.

While the embodiments of the application are susceptible to various modifications and alternative forms, specific embodiments are provided as examples in the drawings and detailed description. It should be understood that the drawings and detailed description are not intended to limit the embodiments to the particular form disclosed. Instead, the intention is to cover all modifications, equivalents and alternatives falling within the spirit and scope of the invention as defined by the appended claims.

DETAILED DESCRIPTION

The automated pill dispensing methods and systems described herein are directed to generating and using plans for dispensing pills into pill packs. Each of these pill packs can have multiple slots for each day, which correspond to different times of the day. The methods process prescription input, calculate the types and number of pill used for each pill pack, and generate a plan. The plan is then used to fill the prescription using a pill dispensing robot.

The pill pack can have a four by seven (or another, such as 4 by 8) slot arrangement. The pill dispensing robot, after dispensing the pills into the pill pack, places a label placed on top of the pill pack. The pill pack can contain a patient name, a picture, and a large amount of information about the contained pills, such as when to take them, and any concerns/side effects with each drug.

As an example, a plan is generated for a pill pack by processing (such as by a computing device) multiple prescriptions for a given patient. The computing device generates a plan template based on the prescriptions, such as for HOA (hours of admissions) of each prescription. The computing device then fills the template to generate a plan for a given patient. The plan is generated to provide an optimal distribution of pills in a single (or even multiple) pill pack.

As an example, the pill dispensing robot can process a pill plan as follows. A pill pack is placed on a round table of the pill dispensing robot. The round table rotates to place the pill pack underneath a dispenser (e.g., a pre-fill tray). The robot processes and fills the prescription, and then dispenses the pills into the pill pack. It is noted that the pill dispensing robot includes a container module (that includes multiple individual containers) for storing and dispensing pills. The container module is configured to dynamically determine the location of each container and type of pills of each container. The table rotates again, where a label is placed onto the pill pack. The table rotates again, where a heat seal presses down onto the label and seals the pill pack. The pill pack is then removed and stored for delivery.

As an example of a pill dispensing robot, one such system can include a supply module, a receiving module, a pre-fill tray, a transfer plate, and a control module. The supply module is configured to supply one or more pills. The supply module includes multiple containers, where each of the containers is configured to dispense one or more pills of a respective type. The receiving module is configured to receive one or more pills from the supply module. The pre-fill tray is configured to receive one or more pills from the receiving module. The transfer plate is configured to receive an arrangement of pills from the pre-fill tray. The control module is operable to control operation of the supply module, the first receiving unit, and/or the second receiving unit.

The pill dispensing robot, by using the pre-fill tray and the transfer plate, separates the pill collection process from the pill dispensing process. By separating these two processes, the selected pills can be collected and stored using the pre-fill tray; while independently, the pill pack can be selected and maneuvered into its place. This separation of processes implements a buffer, that allows the pills to be selected and dropped into the pre-fill tray, without needing to line up the pill pack for each element, and without needing to wait for each such element to be filled (i.e., as each pill selection is dropped into a corresponding pill element of the pill pack). Once the pill pack is lined up (e.g., underneath the transfer plate), the pills are dropped from the pre-fill tray onto the transfer plate. In one embodiment, the pills are automatically transferred from the transfer plate onto the pill pack. In another embodiment, another set of doors can be implemented by the transfer plate, thus having another buffer/transition area between the supply of the pills and the pill pack.

It is noted, that without this pre-fill tray/transfer plate combo, typically there is an inherent delay for the pill pack to be lined up, the pills to be selected, dropped, and even verified to be properly dropped into the pill pack. Instead, the separation of the pill collection process from the pill dispensing process both speeds up the overall operation, and also allows for an easier and more accurate transfer of pills into the pill pack(s). It is also noted that the transfer plate is used as the dimensions of the pill pack can be different from the dimensions of the pre-fill tray. Instead, the dimensions of the transfer plate typically correspond to the dimensions of the pill pack.

A plan generation module accesses a plan, where the plan indicates a first pill distribution for a first time period, and a second pill distribution for a second time period. The plan generation module receives an input, where the input indicates a desired change to the plan. The input also indicates additional pills to be distributed in the first time period. The plan generation module determines whether to modify the first pill distribution or the second pill distribution. In response to a determination that the second pill distribution is to be modified, the plan generation module modifies the plan to indicate changes in both the first and the second pill distributions.

FIG. 1A is a block diagram of a pill dispensing robot 100, according to one or more embodiments. The pill dispensing robot (also referred to simply as a robot 100) includes a supporting section 102, a machine body 104, a canister module 106, and a dispensing portion 108. Robot 100 also includes a pill pack delivery subsystem 110 for delivering pill packs to dispensing portion 108. Robot 100 also includes a computing device 122(1) for controlling robot 100 operation. Robot 100 can communicate with a computing device 122(2) to receive plans for robot 100 operation. Computing device 122(2) is configured to generate and/or modify plans for operation of robot 100.

Computing device 122(1) and 122(2) can be any type of a personal computer, a server, a mobile device, a personal assistant, and the like, including a device having memory for storing one or more applications and one or more processors.

In one embodiment, computing device 122(1) and 122(2) can be implemented using the same computing device.

Computing device 122(2) can execute (e.g., by using the one or more processors) a plan generation module 126 to access, generate, and/or modify a plan 126. Plan 126 indicates a pill distribution by robot 100. Plan 126 is then communicated to a control module 128, which can be executed by computing device 122(1) (e.g., by using one or more processors). Control module 128 processes the plan and controls the robot in accordance with the plan. Various embodiments of using such a control module and plan generation module are described with reference to the Figures below.

Robot Operation

Pills are received and stored by canisters that are stored by canister module 106. Canister module 106 (as also described in more detail in FIG. 3, is configured to hold one or more canister trays, each canister tray being able to receive multiple canisters). Each canister can hold one or more pills of the same type. Furthermore, robot 100 can include an extra pill dispenser 120 (also referred to as an exception tray 120), where a user can manually place pills. Canister module 106 is configured to automatically recognize a type of a pill canister (and thus the type of pills stored by that pill canister), regardless of that canister's location in canister module 106.

Machine body 104 is configured to receive pills from canister module 106. The pills are selected by robot (from canister module 106), as controlled by control module 128 according to plan 126. Machine body 104 processes the pills and places the processed pills in dispensing portion 108 (e.g., including a prefill tray, as discussed below). The pills are then dispensed (e.g., dropped) from dispensing portion 108 into pill packs 112. Dispensing portion 108 dispenses pills to be distributed according to plan 126. As shown, robot includes a rotating table 110 that rotates pill packs 112 around in order to fill these pill packs 112.

Figure 1B:
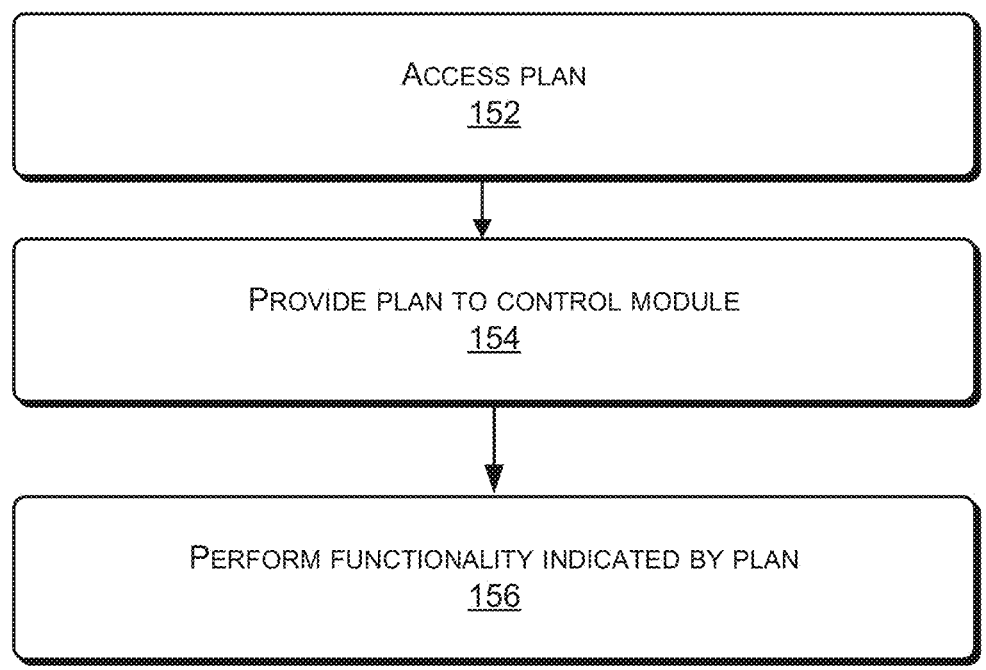
FIG. 1B is a block diagram of a method for generating and executing a dispensing plan for a pill dispensing robot, according to some embodiments.

FIG. 1B is a flowchart illustrating a method of general use of robot 100, according to one or more embodiments. It is noted that the flowchart of FIG. 1B can be performed by one or more modules that access robot 100. As will be appreciated in light of the present disclosure, this method may be modified in order to derive alternative embodiments. Also, the steps in this embodiment are shown in sequential order. However, certain steps may occur in a different order than shown, certain steps may be performed concurrently, certain steps may be combined with other steps, and certain steps may be absent in another embodiment. Method 150 is described with reference to variations of the elements described in connection with FIG. 1.

In element 152, a plan generation module (e.g., plan generation module 124) accesses a plan. The plan can be a new plan, in which case the plan generation module generates a new plan. The plan can be an existing plan, in which case the plan generation module modifies the existing plan (or generates another plan based on the existing plan). The plan generation module can receive input (such as user input) that modifies the existing plan. Various embodiments of plan generation and modification are described below, such as with reference to FIGS. 16-23.

Figure 23:
FIG. 23 is a block diagram of an example pill pack that is filled by the robot, according to one embodiment.

However, in general, a plan indicates distribution of pills by a robot into a pill pack, such as a pill pack of FIG. 23. The pill pack is typically organized by hours of administration (HOA) that includes, for example, the amount of a first drug that is to be administered to a patient in a morning time slot, the amount of a second drug that is to be administered to the patient in the same time slot. The pill pack also includes similar pills that are distributed and labeled for use during other time slots. The plan generation module is configured to receive input from a user that modifies the distribution, type, and number of pills as indicated by the plan.

In element 154, the plan is provided to the control module (e.g., control module 128 of FIG. 1A). Depending on the implementation, the plan can be provided using a network, memory (if both the plan generation module and the control module are implemented using the same computing device), using some memory medium (e.g., a tangible memory storage medium), or using another technique.

In element 156, the robot performs the functionality as indicated by the plan. With reference to FIG. 1A, robot 100 selects one or more pills, according to the plan, from the canister module. The pills are then processed (e.g., propagated using the robot's machine body), and then the selected pills are arranged using the dispensing portion. Once the robot determines a proper position of a pill pack, the selected pills are then dispensed onto the pill pack.

The disclosed embodiments also include a unique robotics system that allows the automation of the packs. The disclosed embodiments also show a distinct approach for optimizing the packaging of medications to significantly reduce the costs of packaging per unit pack per patient. This feature lowers costs for health care to providers and consumers.

A robot packing system to create a customized or modified medicine pack (also referred to as a pill pack) is disclosed. The robot packing system includes a drug cartridge (i.e., a canister) having at least one medicine. The robot packing system also includes a hopper configured below the drug cartridge to receive the at least one medicine. The robot packing system also includes a drop tray having a door for receiving the at least one medicine. The robot packing system also includes a transfer plate to receive the pills released from the drop tray and to place the pills into a holder according to a customized or modified dosage schedule. The robot packing system also includes a sealing station to seal the holder to form the medicine pack. The medicine pack is configured to provide the at least one medicine according to the dosage schedule.

Figure 1C:
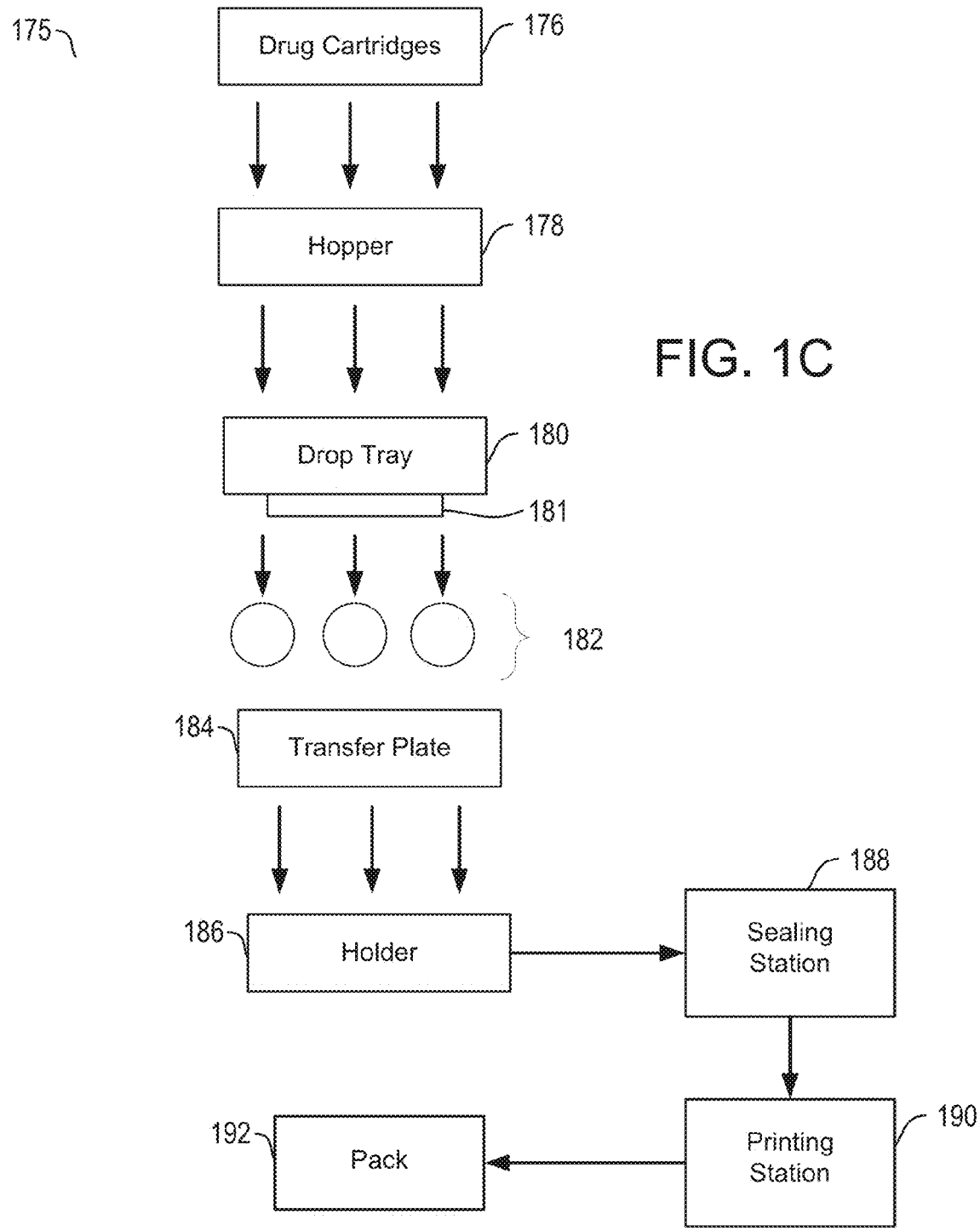
FIG. 1C is a block diagram illustrating general operation of a pill dispensing robot, according to some embodiments.

Some embodiments of the robot packing system are disclosed by FIG. 1C. Robot packing system 175 may be located within a pharmacy, hospital, rehabilitation center and the like where medicines are dispensed. Once a creation, customization, or modification of medicine dosage is received, then the medication packs may be assembled according to the desired configuration. The medication packs can be also assembled simply by accessing existing data.

Drug cartridges 176 (aka pill containers) are located at the top of robot packing system 175. Drug cartridges 176 may include the medicines requested by a patient and selected from an inventory. Drug cartridges 176 also may be located on the sides. This configuration gives flexibility of easy operation for the online changing of the drug cartridges. Drug cartridges 176 can be stored using canister trays.

Drug cartridge 176 may be rectangular with a cylinder underneath. Medicines slide into several channels on the edges of the cylinder of drug cartridge 176 or hopper 178. Rotation of the drug cartridge (such as each drug cartridge rotating to line up with a canister door) causes channels to pass over a hole. An optical sensor ensures only one pill, or medicine, drops as a channel is over a hole. These commands relate to the customizations or modifications selected by the patient according to the disclosed embodiments.

Drug cartridge 176 also includes radio frequency identification (RFID) tags for easy inventor and identification. The RFID relates to a different drug or medicine. This allows the robot to check that the medicine dropping from drug cartridge 176 matches the one indicated by the disclosed customization or modification (e.g., by the plan). RFID sensors of the robot detect which canister, or cartridge, is where within the system. A light emitting diode (LED) may be included and flashes when drug cartridge 176 is empty. A brushed direct current (DC) motor may move cartridges.

The medications fall from drug cartridges 176 into hopper 178. Hopper 178 may go from a wide opening to a narrow bottom opening. The bottom opening may be a square having a length of about 4.25 inches to accommodate placing medications into drop tray 180. From hopper 178, the medications fall to drop tray 180. Drop tray 180 includes a door 181 so that the medicines fill up the tray before the next step. Hopper 178 channels medications to drop tray 180. Hopper 178 may be acrylic and of a clear or a transparent color to allow a user to look into it.

Drop tray 180 may be of a black or dark color with a matte surface. This feature allows drop tray 180 to be used for image processing. A camera takes photos or video of the medicines as they accumulate on drop tray 180. Drop tray 180 also holds the medicines temporarily while an x-y table moves to the required slot while the medicines are dropping. This increases the speed of packaging the medicines. The disclosed embodiments do not have to wait for the required slots to be in position before dropping the medicines. This configuration also may include a servo motor to open and close door 181 along with a door shaft connected thereto. A drop door box may enclose this entire assembly.

The above configuration also may include a small hopper to receive the medicines dropped by drop tray 180. A tunnel may be connected to the small hopper. The tunnel has a certain height that prevents medicines from bouncing back into the small hopper when it is dropped into the pre-fill tray. The tunnel includes a tunnel wall that prevents medicines from slipping into another slot. The tunnel opening should be smaller than the slots in the pre-fill tray, so the tunnel wall covers the top of a slot opening to prevent medicines from falling or bouncing out.

In one embodiment, the prefill tray includes a specified number of slots, such as about 28 slots. The medicines are held here until dropped into the blister packs. The pre-fill tray includes a pre-fill tray door to hold the medicines.

When cavity holder, or blister pack (i.e., a pill pack), moves beneath transfer plate 184, the pre-fill tray door opens to drop medicines 182. Preferably, medicines 182 are a plurality of pills. Medicines 182 also may be known as medicine doses. As stepper motor may drive the pre-fill tray door. Transfer plate 184 allows robot packing system 175 to fill many different packs or vials. Transfer plate 184 packs a cavity holder 186. The dimension of slots in the pre-fill tray is different from the dimension of slots in the blister pack. So transfer plate 184 is needed. Transfer plate 184 has small tubes which will direct medicines 182 to fall from the pre-fill tray into the slots of the blister pack, or cavity holder 186.

Once medicines 182 fill cavity holder 186, the package is forwarded to sealing station 188. A round table configuration may facilitate this process. The round table may have a diameter of about 56 inches and driven by a stepper motor. It may include about 5 sections/tray slots. Sealing station 188 may located on the right side of the round table. One or more infrared photodiodes may ensure accurate turning of the round table. The photodiodes also detect the packs on the round table, and automatically raise a warning if a pack is not present when medicines are dropped.

The round table also includes manual controls to manually turn the table as needed. The controls may move the table left or right. The manual controls also include a manual control for heat sealing the package. Thus, an operator may perform the process manually as opposed to automatic. The controls also include an emergency heat seal release.

The package is heat sealed in order to keep the medicines stable and to prevent spilling the contents. Sealing station 188 does this. Sealing station 188 may use a step-based actuator. An emergency release button may be included on sealing station 188 along with an openable cover to prevent accidents. A laser curtain on openings of the cover detects when a hand is near in order to shutdown and prevents injury. The package is then sent to printing station 190. Pack 192 can be made available at the pharmacy, hospital and the like for pick up by the patient.

Figure 2E:
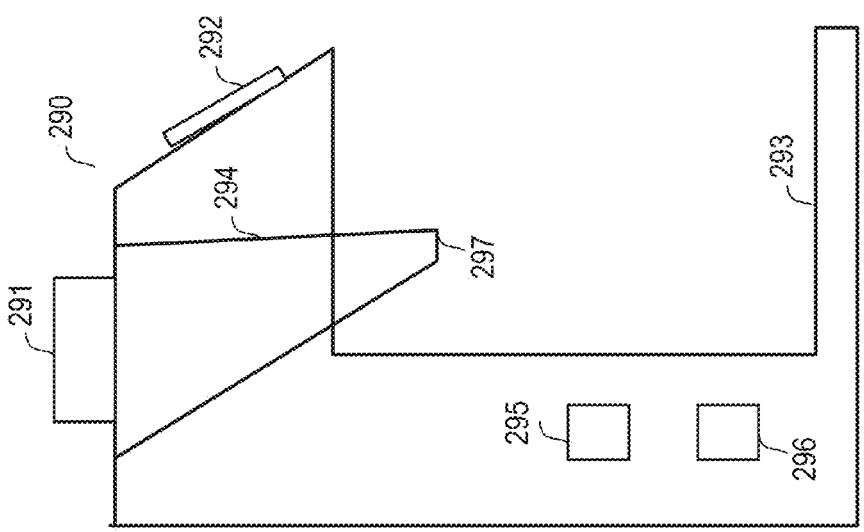
Figure 2A:
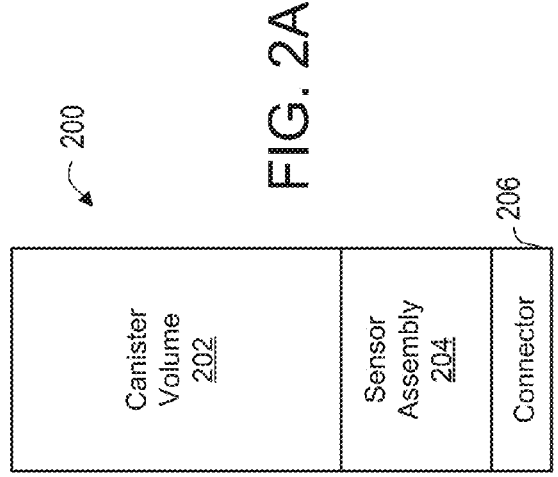

FIGS. 2A-2E are block diagrams of various elements used by a canister module, such as canister module 106 of FIG. 1, according to some embodiments. FIG. 2A illustrates a general block diagram of a canister 200 that is used by the pill dispensing robot, according to one embodiment. Canister 200 includes a canister volume 202, a sensor assembly 204, and a connector 206. As described above, a canister module typically includes multiple canisters (each of which can be implemented using canister 200). Each of these canisters can be mounted on a canister receiving module (such as described with reference to FIG. 2B).

Sensor assembly 204 can include, as shown in FIG. 2C, a scanner 252 and a sensor 254. Sensor assembly 204 is configured to indicate the type of pills for canister 200. Scanner 252 is configured to receive signals from sensors 254 that indicate a type of pill that is contained by canister volume 202. Connector 206 is configured to interface with canister receivers of the canister module.

FIG. 2B illustrates a canister tray 225, according to one embodiment. It is noted that a canister module (e.g., of FIG. 1A) can include multiple canister trays 225. Canister tray 225 includes multiple canister receivers 228(1)-212(n). In one implementation, canister tray 255 can hold 16 canisters by using three rows, with four canisters per each row. However, other canister receiver layouts are contemplated. Each of canister receivers 228 includes a sensor. The sensor is configured to receive communication (e.g., wireless communication) from the sensor assembly of the canister. The sensor thus can be implemented using RFID, Bluetooth, NFC, and/or any other low-power wireless technology. For example, the canister can transmit (e.g., using its sensor assembly) communication that indicates the type and number of pills contained by that canister. This communication is received by a sensor of a corresponding canister receiver of canister tray 225.

Furthermore, a canister module (e.g., of FIG. 1) can include multiple canister trays. Each such canister tray can be coupled together, such as via a coupling element 230. If canister trays are mounted on top of each other, then coupling element 230 can also allow pills to pass through, i.e., to the hopper. Thus, coupling element 230 can provide both structural support (i.e., for mounting one tray on top of another) as well as for transporting pills. In another implementation, canister trays are mounted next to each other. In this implementation, the pills that are dropped from each canister tray can be all merged into the same hopper.

In one embodiment, each exception tray can have substantially the same dimensions as each canister tray. As a result, each slot of the exception tray can hold pills that are dropped to a corresponding slot of the canister tray. This simplifies the operation, as a user (e.g., a technician) can place pills into a certain slot of the exception tray (e.g., as prompted (e.g., via a GUI) by the control module)).

Pills can be placed in a container in a variety of ways. A refill device (such as a refill device 290 of FIG. 2E) can be used to place pills in a canister. The refill device can count the number of pills dropped (such as by a user or by another machine) into a container. The refill device can then communicate with the control module with the number of pills in a particular container. In one embodiment, refill device 290 includes a canister drier 291, a display/indicator 292, a canister base 293, a hopper 294, one or more processors 295, memory (including a refill control module, executable by processor(s) 295) and hopper opening 297, among others. It is noted that refill device 290 can include additional (or fewer) elements, as desired.

A canister is placed on canister base 293 such as to line up an opening of the canister with hopper opening 297. However, pills can be placed into hopper 294 without the canister being present, as hopper opening 297 can include a door is closed (as controlled by the refill control module) until the canister is placed on canister base 293. Display/indicator 292 can indicate to a user the amount of pills present in each canister, the amount of pills being placed into hopper 294, and/or whether the canister is lined up properly underneath hopper opening 297. The refill control module can be used to add a canister, modify the number and/or type of pills in a given canister, assign a new id (e.g., an RFID) to a canister, assign a new id (e.g., an RFID) to a certain pill type, among others.

For each canister that is placed on the canister base, the refill control module can determine (such as by communicating with the robots control device and/or reading some information from that canister) the amount of pills present in that canister. For a new canister, there may not be any pill type or pill number associated with that new canister. For a previously used canister, the refill control module can access the type and number of pills (which may be zero or close to zero) associated with that canister. The refill device determines the type of pills held by each canister, such as by reading that canister's RFID tag (or another type of a tag, depending on the implementation). Furthermore, a barcode for the pills can be scanned, and then the RFID and the barcode (or another type indication, such as NDC (national drug code)) is transmitted to the control module.

If the pill type is not changed (which can be performed, such as by accessing display/indicator 292), the refill control module can add the number of pills dropped into hopper 294 (and thus later into the container) to the number of pills that was stored by that container prior to the container being placed in refill device 290. This total number of pills is then communicated to the control module (such as to an inventory module and/or a queue manager).

FIG. 2D illustrates a canister drive module 276, according to one embodiment. Canister drive module 276 (which can implement each one of canister receivers 228) includes a canister door 278, a canister base 180, a transmitter 282, one or more photodiodes 284(1) and 284(2), a scanner 286, and a sensor 288. A canister can physically attach (e.g., using connector 206) to canister drive module 276 by mounting on canister base 280 (such as by using any of physical connector(s)). Sensor 288, which can be implemented using a push button, senses if the canister is present. For example, if the canister is present, the push button is pressed, which can be indicated to the control module. Similarly, if the canister is not present, the push button is not pressed, which is also indicated to the control module.

Scanner 286 interfaces with a sensor on the canister (such as sensor 204). Scanner 286 can be implemented using a variety of technologies, such as RFID, Bluetooth, NFC, among others. Transmitter 282 and receiver (e.g., implemented using a photodiode 294) can be paired together to detect if there's a canister mounted. Canister door 278, which are opened and closed using a stepper motor, as instructed by a control module, allow pills to fall into a hopper (such as hopper 178). Alternatively, the stepper module can rotate the canister to line up with canister door 278 to drop the pills.

In one implementation, the control module of the robot receives communication from canister tray 225 to dynamically determine the type of canister, and thus the type of pills, present at each canister location. For example, the control module can determine that canister A is present at location 228(1) and canister B is present at location 228(2). Canister A can contain pills of type A, and canister B can contain pills of type B. During operation of the robot, various canisters can be attached to canister tray 225 at different times. The robot's control module can dynamically determine the type of pills at each canister location (of canister tray 225). The robot can distribute the pills into packs according to the plan, by dynamically determining which canisters to use at which time. As the canisters can be attached to various locations at different times, a canister with pills of type A can be attached at location 228(1) at the beginning of execution, and at location 228(2) at another time.

In other words, by using the canister sensor assembly and the sensors on the canister tray, the control module can determine the location of each canister type. The users are also not limited to attaching the same canister type in the same location on the canister tray each time. Furthermore, the canister tray is configured to accept (and register with the robot's control module) various different types of canisters that hold various different types of pills at different locations on the canister tray. This dynamic canister allocation allows the robot to populate pill packs using a variety of different pills.

The robot can indicate, such as using a user interface (UI), such as a graphical UI (GUI) to a user that a certain type of pills is missing/running low. The canister tray can determine such pill using the sensor assembly combo. In one embodiment, the canister tray can include additional sensors, such as camera(s), weight scales, or other techniques to determine the amount of pills in each canister. These additional sensors can determine the amount of pills left in canister volume 202 of canister 200.

In one embodiment, the canister tray (and optionally, the canister assembly itself) can include a processor and memory. This memory holds a control program that monitors the type and/or number of pills in each canister and at each canister receiver location. In one implementation, the canister assembly includes a visual indicator, such as an LED and/or LCD, that informs the user of the type/status of the pills in each canister. For example, the visual indicator can indicate, using a predetermined color (such as emit a yellow light) and/or visual message that the amount of pills is running low. Similarly, the visual indicator can indicate, such as by emitting a green light, that a given canister has a sufficient amount of pills (where the amount of pills for being considered sufficient can be determined by the amount of those types of pills being used by the pill dispensing jobs in the queue of the robot). The visual indicator can indicate, such as by emitting a red light, that a given canister does not have a sufficient amount of pills, or even that this canister is out of pills.

In another embodiment, the sensor assembly and/or canister tray monitor acquire information about the canisters, and then transmit this information to the robot's control module. The control module then processes this canister information correspondingly. The control module can indicate back to the canister assembly information regarding the type and/or amount of pills, such as if a certain canister doesn't have an amount or type of pills needed for a plan that is currently being implemented.

The canister tray can have a trap door, or some other element, to release a pill from each canister. In one implementation, each canister receiver in the canister tray can include a trap door, or another implementation, where one or more pills from that canister are dropped (or pressure pulled) into the machine body. The control module selected what pill to drop into the machine body at what time based on the plan. The canister tray is configured to drop one pill at a time. In one implementation, the control module can control the drop door of each canister receiver to select the number of pills that are being dropped (or otherwise transported) from each canister to the machine body.

FIGS. 3A and 3B are block diagrams of a machine body of a robot, such as machine body 104 of FIG. 1. FIG. 3A illustrates machine body 300 that includes a hopper element 302, a transport element 304, a pre-fill element 306, and a transfer element 308.

In some embodiments, machine body 300 receives one or more pills from a canister tray (of a canister module). As shown in FIG. 1, the canister module is typically physically located substantially above machine body 300. This location of machine body allows pills to be transported using gravity from the canister module to machine body 300. However, other implementations are contemplated, including where the selected pill(s) are transported from the canister module to machine body using one or more air pressurized tubes, or other techniques. Regardless of the pill transport mechanism used between the canister module and machine body 300, each pill is selected from the canister module by the control module as described above (e.g., using the sensor and sensor tray to determine the type of pills at each location in the sensor tray).

The pill(s) can be selected one type at a time. For example, the control module can select one pill, or multiple pills of the same type, to be dropped into hopper element 302. In one implementation, if a certain type of a pill that is to be administered at the same HOA would take up more than one entry in a pill pack, then the control module only drops enough pills at a time for a single entry in the pill pack, regardless if additional pills are being used for the same HOA and pill pack. The remaining pills are allocated to another slot in the pill pack.

The selected pill(s) are transported from hopper element 302 to a dispensing portion, which includes a transport element 304, prefill element 306, and transfer plate 308. The selected pill(s) are thus transported from hopper element 302 using transport element 304 to a pre-fill element 306. Prefill element 306 stores selected pills according to the plan being processed by the control module. In one implementation, prefill element 306 stores pills for each day (e.g., such as for each column of the pill pack). In another implementation, prefill element 306 stores pills for the same HOA for all the days (e.g., such as for each row of the pill pack). In either implementation, once the pills for the row (or alternatively, for the column) are stored by pre-fill tray 306, pre-fill tray 306 drops the pills onto transfer plate 308.

Pre-fill element 306 can be moved (such as by using an x-y motor) to receive pill(s) for each entry in the pre-fill element. For example, at time t=1, pills of type A are dropped into element A of pre-fill tray. At time t=2, pills of type B are dropped into element B of pre-fill tray. Pre-fill element 306 can be moved, translated, and/or rotated to align a certain element of pre-fill tray with transport element 304.

Figure 4:
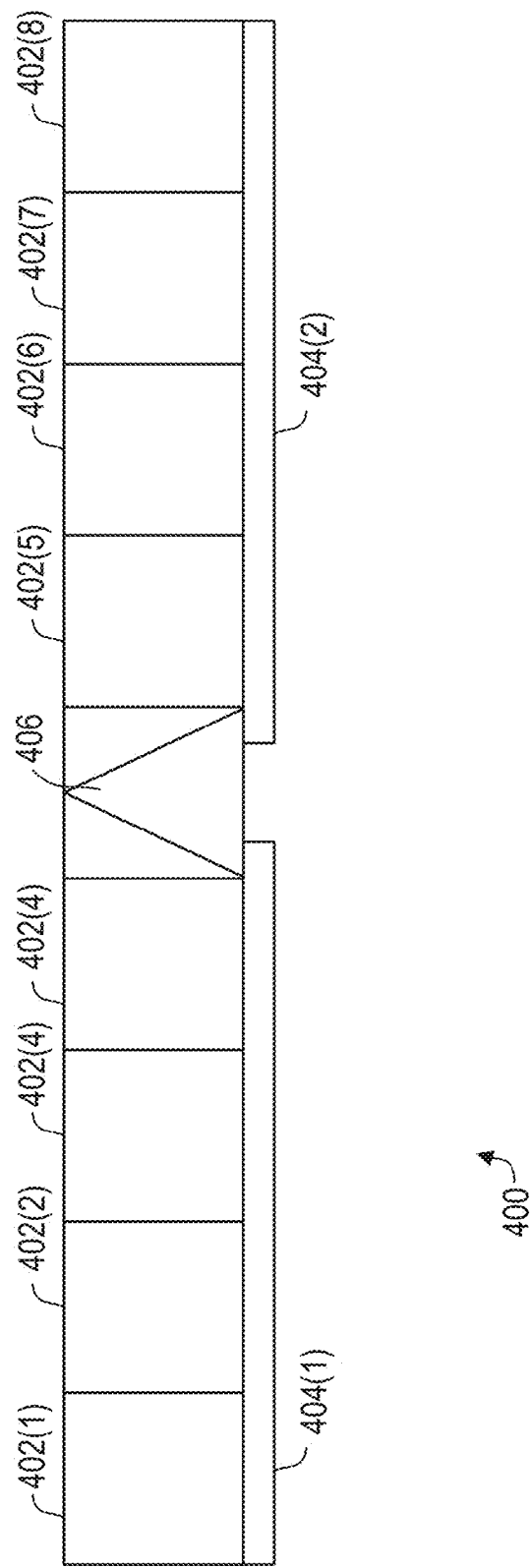
FIG. 4 is a block diagram of a pill holding element of the pill dispensing robot, according to some embodiments.

Transfer plate 308 is configured to store pills that will be transported onto the pill pack. In one embodiment, transfer plate 308 includes a sliding door or another mechanism that can transfer the held pills onto the pill pack. One implementation of such a pre-fill element is shown in FIG. 4. Furthermore, since the robot is using separate pre-fill tray and transfer plate elements, pre-fill tray can be populated with pills for plan B, while the transfer plate is waiting to transfer its pills (populated for plan A) onto a pill pack.

FIG. 3B is a detailed view of one embodiment of machine body 300 of FIG. 3A. FIG. 3B illustrates a main hopper 352, a camera attachment element 354, a camera 356, a motor 358, a door shaft 360, a drop door 362, a drop box 363, a small hopper 364, a tunnel 366, a tunnel wall 368, a pre-fill tray 370, a pre-fill tray door 372, a motor 374, and a transfer plate 376.

Generally, the robot packing system (such as described above with reference to FIG. 1C) shows the system after the medicine is released from the canister, or the drug cartridge. Here, main hopper 352 receives the medicine and channels them to drop door 362. Camera stand 354 supports a camera 356, which may be used for quality assurance or counting operations, as disclosed above. Main hopper 352 may be transparent.

Medicines, preferably in the form of pills, accumulate on drop door 362. Servo motor 358 opens and closes drop door 362 when the packing system gives the instructions to release the medicines. Door shaft 360 connects servo motor 358 and drop door 362 and actuates drop door 362. Drop door box 363 is a square box that encloses the drop door assembly.

Small hopper 364 channels medicine released from drop door 362 into small tunnel 366. Tunnel 366 and tunnel wall 368 (which can be also implemented as a flange extending outward from tunnel 366) prevents medicine from jumping into another slot or falling away. Pre-fill tray 370 holds medicines before they are dropped into the pack. Pre-fill tray doors 372 and 374 hold the medicines until instructions are received from the control module to release. Stepper motor 374 drives pre-fill tray doors 372 and 374. Doors 372 and 374 release when transfer plate 376 is above the medicine pack and below pre-fill tray 370.

Other configurations of the robot packing system may be used according to the disclosed embodiments. For example, transfer plate 376 may reflect the customized or modified dosage schedule desired by the patient. Additional details and/or embodiments are described below.

In one embodiment, elements of main hopper 352, a camera attachment element 354, a camera 356, a motor 358, a door shaft 360, a drop door 362, a drop box 363, and a small hopper 364 can implement the hopper element 302 of FIG. 3A. In one embodiment, elements of tunnel 366 and tunnel wall 368 implement transport element 304. In one embodiment, elements of pre-fill tray 370, pre-fill tray door 372, motor 374 implement pre-fill element 306. In one embodiment, transfer plate 376 implements transfer element 306.

In the embodiment shown by FIG. 3B, one or more pills are dropped into main hopper 352 from the canister module, as instructed by the control module of the robot. Door shaft 360 can be used to control the opening and closing of drop door 362.

Camera attachment element 354 attaches an optional camera 356. Camera 356 can be used to verify (by communicating with the control module) that the selected pills are dropped into main hopper 352. If the wrong pill(s) are dropped, depending on the implementation, the control module can indicate to a technician that wrong pills are dropped (such that this batch of pills is corrected/thrown away before the pill pack is finalized). In another implementation, if it is detected that the wrong pills are dropped, the control module can direct the wrong pills into a wrong pill receiving element (not shown). If not enough pills are dropped, the control module can instruct the canister module to drop additional pill(s). If too many pills are dropped, the control module can direct all of the pills into the wrong pill receiving element, and redo the selection and drop of these pills.

The pills are dropped from main hopper 352 onto drop door 362. The pills are held on the drop door 362 until the control module directs drop door 360 to open (such as by directing motor 358 to move/rotate door shaft 360). However, other techniques for opening drop door 362 are contemplated. Furthermore, due to the use of drop door 362, the pills can be dropped into main hopper 352 while the pre-fill tray is being moved into a proper position.

Small hopper 364 is configured to channel the pills from drop door 362, through tunnel 366, onto pre-fill tray 370. Pre-fill tray 370 typically includes the same number of slots as the pill pack. Furthermore, the opening of tunnel 366 and tunnel wall 368 is typically large enough for one slot of pre-fill tray 370 to be exposed to the pills being dropped from tunnel 366. Pre-fill tray 370 is moved (e.g., translated in the x-axis and/or in the y-axis) to line up a desired slot of pre-fill tray 370 with the selected pills being dropped through tunnel 366. The control module is configured to select the pills and line up pre-fill tray 370 to fill slots of pre-fill tray 370 according to plan.

In one embodiment, when a required number of pills of a first type have been dropped into their respective slots of the pre-fill tray, drug cartridge 176 is exchanged (e.g., by rotation of a carousel of such cartridges) for a different drug cartridge, and pills of a second type are dropped into the pre-fill tray. This can be repeated for a third and fourth drug, etc., until all the drugs in the plan have been collected in pre-fill tray 370.

Once slots of pre-fill tray 370 are filled with pills according to the plan, the control module is configured to open pre-fill tray door 372 using motor 374. As described in more detail in FIG. 4, pre-fill tray door 372 can be implemented using two doors, which can be pulled open (e.g., in opposite direction) by motor 374. Pills are then dropped from pre-fill tray 370 onto transfer plate 376. Transfer plate 376 is used to transfer pills to the pill pack, as the dimensions of the pill pack can be different from the dimensions of pre-fill tray 370. In one implementation, transfer plate 376 guides the transfer of pills from pre-fill tray 370 onto the pill pack, such as by including small tubes that direct the pills falling from pre-fill tray 370 onto the pill pack.

The cross-sectional profile of each hole in the transfer plate may progressively change from top to bottom so that, at the top, pills of different shapes and orientations can be received, and at the bottom the pill or pills is/are presented in a preferred orientation in a slot of the pill pack. In one embodiment, the control module can select a different transfer plate depending on the type and dimensions of the pill pack being used. In this embodiment, transfer plate can be automatically selected out of multiple transfer plates, such as sliding one transfer plate for use, and sliding another transfer plate out.

FIG. 4 is a block diagram of a pre-fill tray 400, such as pre-fill tray 370 and/or pre-fill element 310, according to some embodiments. Pre-fill tray 400 includes elements 402(1)-402(8), each of which is configured to hold one or more pills. Pre-fill tray 400 also includes doors 404(1) and 404(2) (also referred to as trap doors), which are pulled open (e.g., away from central element 406). Upon opening of doors 404, pills that are stored by elements 402 are dropped, such as onto a transfer plate. In this implementation, elements 402 are arranged (if looked from a top view) as a single row or a single column that corresponds to a single row or a single column of elements of a pill pack, such as a pill pack of FIG. 23.

In one implementation, pre-fill tray 400 includes elements 402 for one row (or for one column) of the transfer plate, and thus of the pill pack. In this implementation, the control module fills the pre-fill tray several times for each pill pack, such as for each column. In another implementation, pre-fill tray 400 includes elements 402 for all rows and columns of the transfer plate, and thus of the pill pack. In this implementation, elements 402 are arranged (if looked from a top view) as a matrix of rows and columns that correspond to elements of a pill pack, such as a pill pack of FIG. 23.

Figure 5:
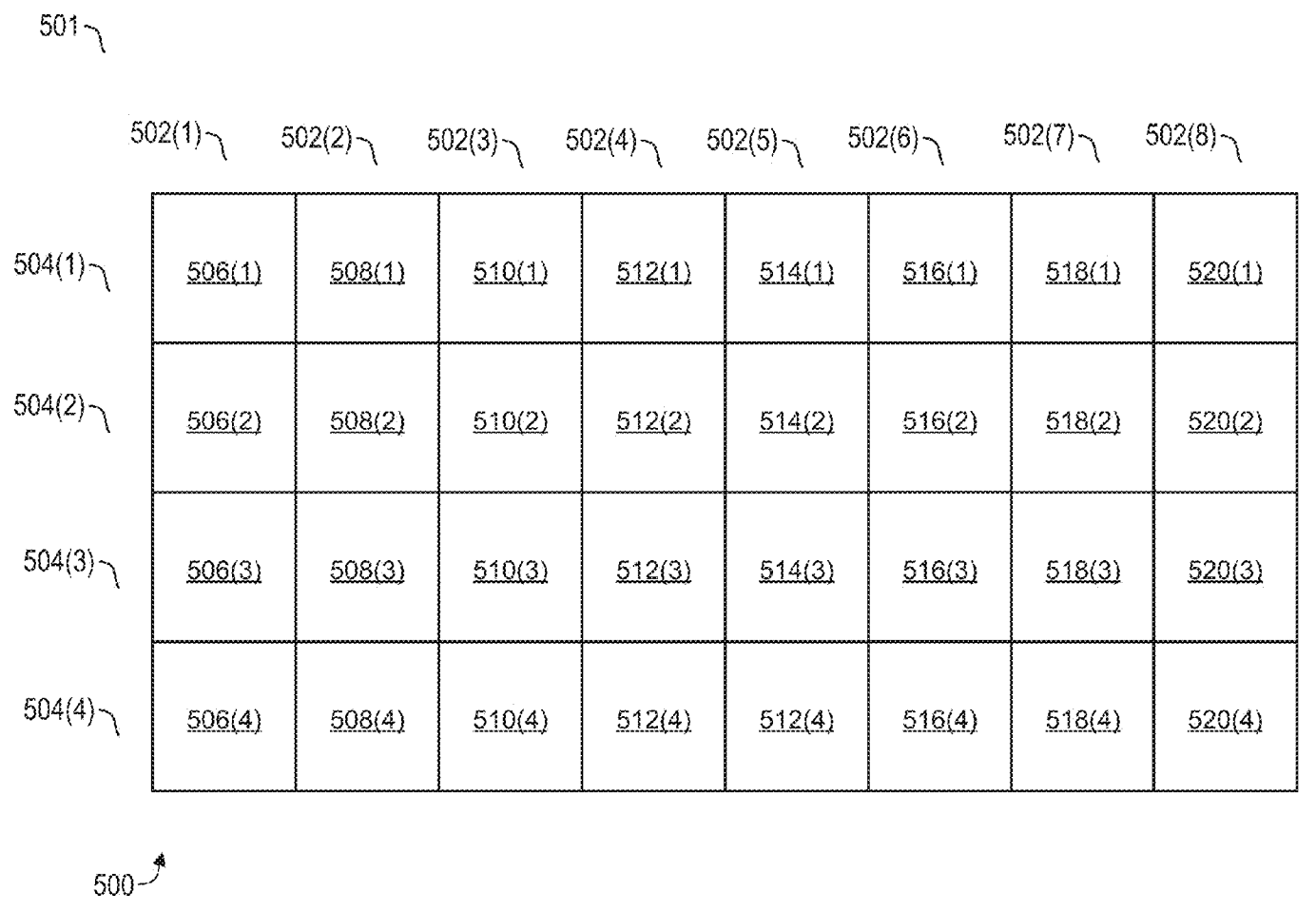

FIG. 5 is a block diagram of a top view of a pill pack 500, according to one or more embodiments. Pill pack 500 includes a plurality of slots 501 that are configured to receive pills from the dispensing portion of the robot, such as from a transfer plate. Slots 501 are arranged in columns 502(1)-502(8) and rows 504(1)-504(4). As illustrated, pill pack 500 includes elements 506, 508, 510, 512, 514, 516, 518, and 520 in rows 502. It is noted that the number of rows and columns is shown for explanatory purposes only, and the actual implementation can have additional, or fewer rows and/or columns, as desired.

Embodiments of the invention permit one or more of slots 501 of pill pack 500 to receive several pills of the same or different types. This can be implemented in one of several ways. In some implementations, each slot of the pre-fill tray receives no more than one pill in a pre-fill tray filling operation. However, in other implementations, each slot of the pre-fill tray receives several pills.

For example, the transfer plate can implement a many-to-one (typically from 2:1 to 4:1) transfer of pills from slots of the pre-fill tray to the slots of the pill pack. This can be implemented by downwardly sloping and converging tubes, or it can be implemented by funnel-shaped holes, each hole encompassing, at its top, several slots of the transfer plate tray and, at its bottom, a single slot of the pill pack. Some holes in the transfer plate may transfer pills on a one-to-one basis, while others in the same transfer plate may transfer pills on a many-to-one basis. In this embodiment, the transfer plate makes a single transfer of pills to the pill pack.

Alternatively, the control module can fill the pre-fill tray, and then instruct the transfer plate to transfer the pills to the pill pack several times for each pill pack, once for each pill of a slot of the pill pack. In this case, if the maximum number of pills in a slot of the pill pack is N, the pre-fill tray is filled N-times.

In another embodiment, the transfer plate holds the pills from several pre-fill tray filling operations, before making a single transfer to the pill pack. In this embodiment, the transfer plate acts as a buffer for several pre-fill tray filling operations. In yet another embodiment, the pre-fill tray holds enough pills for each pill pack, and then these pills are transferred to the transfer plate, and then to the pill pack (once the pill pack is lined up).

In general, FIG. 5 depicts an improved packaging configuration of patient-customized medications according to the disclosed embodiments. The number of packs may be reduced using the above methods and processes. Here, pack 500 can hold the medication dosages as determined by the plan generation module of Figure to improve convenience for the patient.

In some embodiments, the medications are dispensed by day slots (rows 504) and time slots (columns 502) created in the packs according to the information provided by the patient. The time slots are created horizontally to enable the patient to take his or her medication based on the preferred schedule. Of course, the columns and rows may be swapped so that the columns represent days and the rows represent times. The time of each time slot can be printed at the head (end) of the respective column (row) by a printing station, which can also print the patient's name and any special instructions. Indeed the entire top face of each pack, with rows and columns to correspond to underlying bubbles or compartments may be printed by the printing station, together with days and times and different graphic representations of different medications (and/or other information specific to the underlying contents), each in a respective row/column intersection. The precise packaging methods disclosed above reduce the excess waste of packs and provide better compliance and efficacy with fewer side effects for the patient.

Furthermore, the control module is configured to accept pill packs of various sizes. The control module can select the appropriate pre-fill tray and associated transfer plate for each pill pack. For example, one set of a pre-fill tray and an associated transfer plate can be chosen for a pill pack having dimensions of 4 rows by 8 columns, and another set of a pre-fill tray and associated transfer plate can be chosen for another pill pack having dimensions of 3 rows by 10 columns. As noted, the pre-fill tray and associated transfer plate can be automatically (e.g., motorized as controlled by the control module) placed into the dispensing portion of the robot, while the previous set of a pre-fill tray and associated transfer plate is automatically taken out of the dispensing portion.

Generally, a transfer plate having $M_1$ rows by $N_1$ columns for a pill pack having $M_1$ by $N_1$ slots, can be exchanged, under automated control of control module 128, for another transfer plate having dimensions of $M_2$ rows by $N_2$ columns. In other words, the pre-fill tray typically is not changed, while the transfer plate can be matched for each pill pack. In this embodiment, the pre-fill tray can have larger dimensions, i.e., that accommodate various transfer plate (and associated pill pack sizes). In this case, the transfer plate may have fewer holes than the pre-fill tray, e.g. the pre-fill tray may have $M_1$ rows by $N_1$ columns and the transfer plate may have $M_2$ by $N_2$ slots, where $M_2$ is less than $M_1$ or $N_2$ is less than $N_1$. In each case the transfer plate is matched to the pill pack.

As noted, the transfer plate can be automatically (e.g., motorized as controlled by the control module) placed into the dispensing portion of the robot, while the previous transfer plate is automatically taken out of the dispensing portion. Note that this ability to mix and match transfer plates to the pill packs provides for great flexibility, without unduly proliferating the number and type of hardware elements required to implement a wide variety of plans.

In one implementation, the prefill tray can have substantially the same dimensions as the pill pack. As a result, each slot of the prefill tray can hold pills that are dropped to a corresponding element in the pill pack. By using a prefill tray that has substantially the same dimensions as a pill pack, transfer of pills is simplified. In one embodiment, the control module can select a transfer plate (from multiple available transfer plates) with dimensions corresponding to a pill pack being used.

Figure 6:
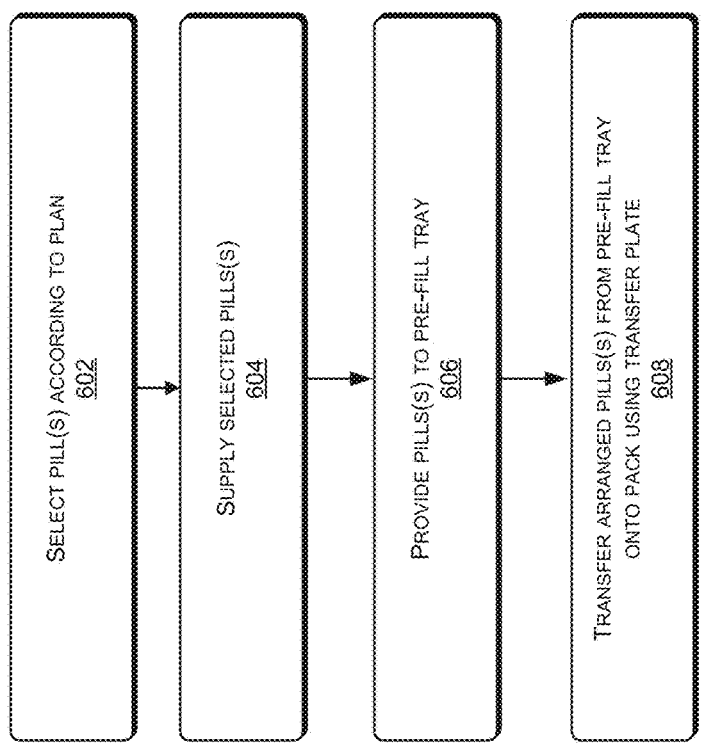
FIG. 6 is a flowchart of a method of operation of the pill dispensing robot, according to some embodiments.

FIG. 6 illustrates a method of operating the robot, according to some embodiments. As will be appreciated in light of the present disclosure, this method may be modified in order to derive alternative embodiments. Also, the steps in this embodiment are shown in sequential order. However, certain steps may occur in a different order than shown, certain steps may be performed concurrently, certain steps may be combined with other steps, and certain steps may be absent in another embodiment. Method 600 is described with reference to variations of the elements described in connection with FIGS. 1-5. In one implementation, at least a portion of method 600 can be implemented and/or performed by a control module, such as control module of the robot, e.g., after receiving the plan from the plan generation module.

It is noted that prior to performing the elements of the plan, the control module can select which plan to perform, such as from a queue (as also described below). In one implementation, the plans can be queued up in a first-in, first-out queue. The plans are then selected based when each plan was queued in relation to the other plans. Some plans can also be prioritized, i.e., placed ahead of other plans in the queue. The prioritization can be based on user input (such as via a GUI), based on a certain plan parameter, or based on availability (or lack thereof) of certain pills in the canister module of the robot. The plans can be selected based on the availability of the pills. The control module receives communication from the canister module indicating the type and location of pills that are currently installed.

In element 602, the control module selects pills according to a plan. The plan can indicate the type, amount, and HOA for each pill used by the plan. The plan can also include other attributes, such as priority of creation of pill pack(s), a number of pill packs to be generated, whether generic (or other alternatives) drugs can be substituted, and the like.

In element 604, the control module supplies the selected pills to the dispensing portion. The control module can send communication, such as instructions and/or commands, to the receiving module (also referred to as a machine body in the Figures). This communication, once received, is used by the canister module to select one or more pills to drop.

In element 606, the pills are provided to the pre-fill element (e.g., a pre-fill plate/pre-fill tray). The control module (or some module of the receiving module) can control the timing and operation of when the pills are transferred from the receiving module to the pre-fill element.

In element 608, the pills are transferred from the pre-fill element to the pill pack using the transfer plate. The control module can determine the timing of the transfer of the pills based on the position of the pill pack with relation to the transfer plate. The control module can control the movement of a moving element (e.g., a round table, a conveyor belt, and the like), including pausing the movement of the moving element to allow the pills to be transferred from the transfer plate onto the pill pack. This transfer of pills can include the control module sending instructions to open the drop door of the receiving module, such as described above.

Figure 7:
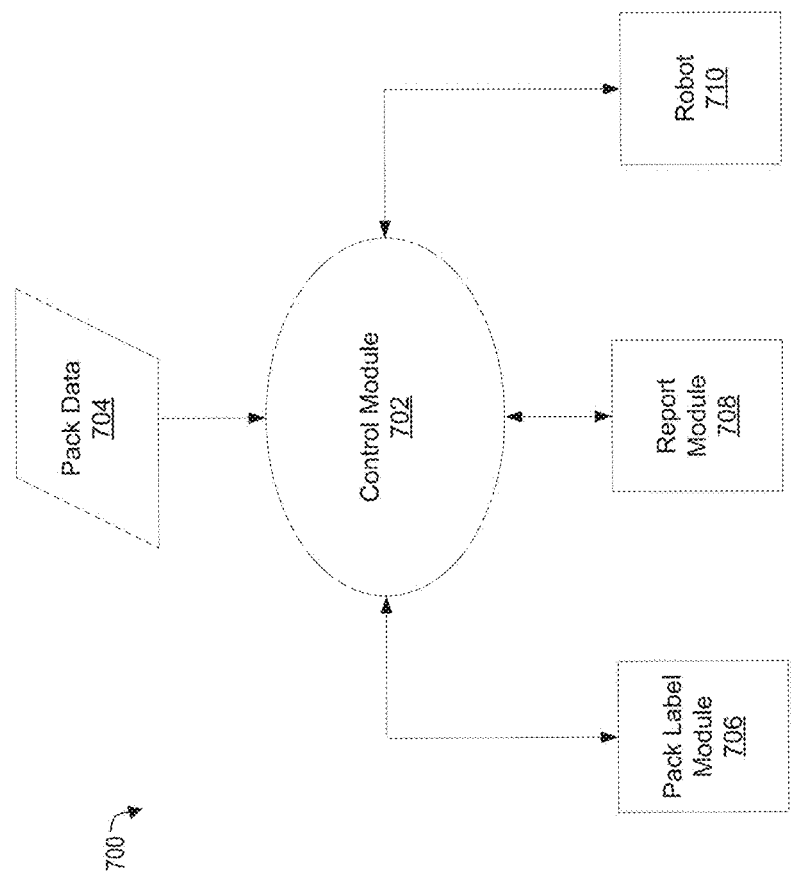
FIGS. 7-12 are block diagrams of various modules and elements used by the control module, according to some embodiments.

FIG. 7 is a block diagram 700 of a control module 702 and supporting modules and elements, according to one embodiment. Control module 702 is configured to receive pack data 704, process pack data 704, and communicate with pack label module 706, generate one or more report module 708, and communicate with robot 710.

Pack data 704 can include one or more plans, as well as other data regarding the pill packs. Pack data 704 can also indicate whether or not alternative drugs are accepted, such as generic drugs. Pack data 704 can also indicate labels that are to be placed on each pill pack.

Pack label module 706 is configured to generate labels that are to be placed on the pill packs, as instructed by the pack data. The labels are typically physically attached to the pill packs after each such pack is filled with the pills (according to the plan). Pack label module 706 typically applies the chosen times for each day of the week. For example, pack label module 706 can label the rows Sunday through Saturday (one row for one day of the week), and label the columns Morning, Noon, Evening, and Bedtime (one column for one HOA time). Furthermore, as shown in the example pill pack of FIG. 23, the label module can merge two of the HOAs into one, such as by labeling two columns with a Bedtime designation (i.e., no evening). Similarly, if the plan for the patient does not indicate any pills for one or more days of the week, and another day required extra pills, the pack data can indicate to label two rows with the Monday designation (and have no Tuesday designation, for example).

Report module 708 is configured to generate reports regarding operation of the robot. The reports can include the type and number of pill packs generated, statistics on the number of type of pills used, the speed of operation of the robot, and the like.

Control module 702 can generate one or more commands that are sent to pack label module 706, report module 708, and/or robot 710. It is understood that the commands can be implemented in various ways, such as using notifications, messages, objects, remote procedure calls, data packets, control signals, and/or other implementations.

Figure 8:
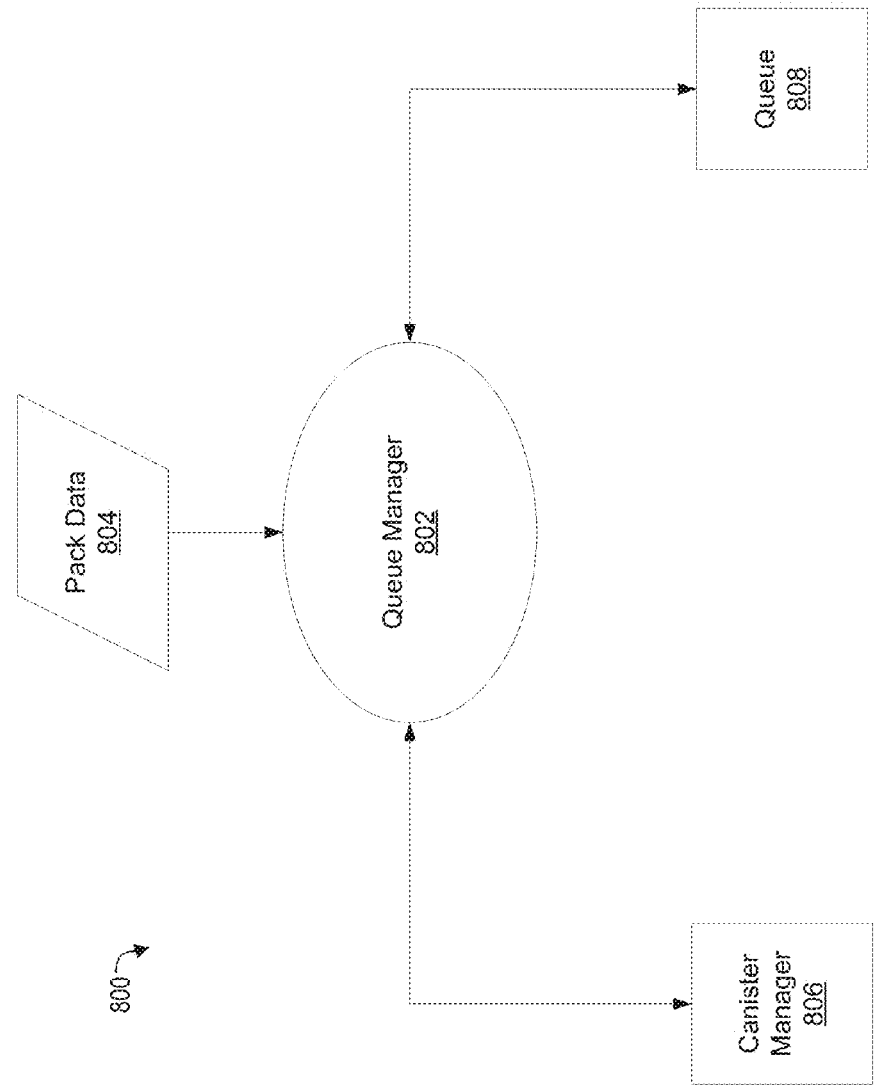

FIG. 8 is a block diagram of a queue manager 802, according to one or more embodiments. Queue manager 802 receives pack data 804 (such as when processing pack data received from a plan generation module). Queue manager 802 then processes the pack data, including the plan, to determine when the plan(s) that are included in the pack data should be processed. Canister manager module 806 can collect and send data about the canisters to queue manager 802. Canister manager module 806 also controls the pill dispensing process, as described above. Canister manager module 806 can receive data for each canister from the refill device, i.e., as each canister is being refilled by the refill device.

Queue manager 802 can use data indicating current conditions from canister manager module 806. For example, if the canister data indicates that a certain type of pill is not present, or that it is scheduled to run out after a certain number of pills are used for other pill packs. Queue manager 802 can receive his data from an inventory manager, such as described below. Queue manager 802 accesses queue 808, such as to obtain the next pill pack to process. Queue manager 802 accesses the next pill pack using first in, first out (FIFO) rules, but exceptions are allowable, such as for a higher priority pill pack, on a lack of availability of a certain type of a pill, etc. Also, other queue scheduling approaches are contemplated, such as LIFO, priority, processor sharing, preemptive job first, shortest remaining processing time, and/or others.

Thus, queue 808 contains pill pack data that are to be processed (i.e., sent to the robot control module and/or to canister manager module 806 for processing. Each pill pack data (such as pack data 804) indicates how canister manager module should dispense pills and how control module should control various components of the robot to generate a pill pack.

Figure 9:
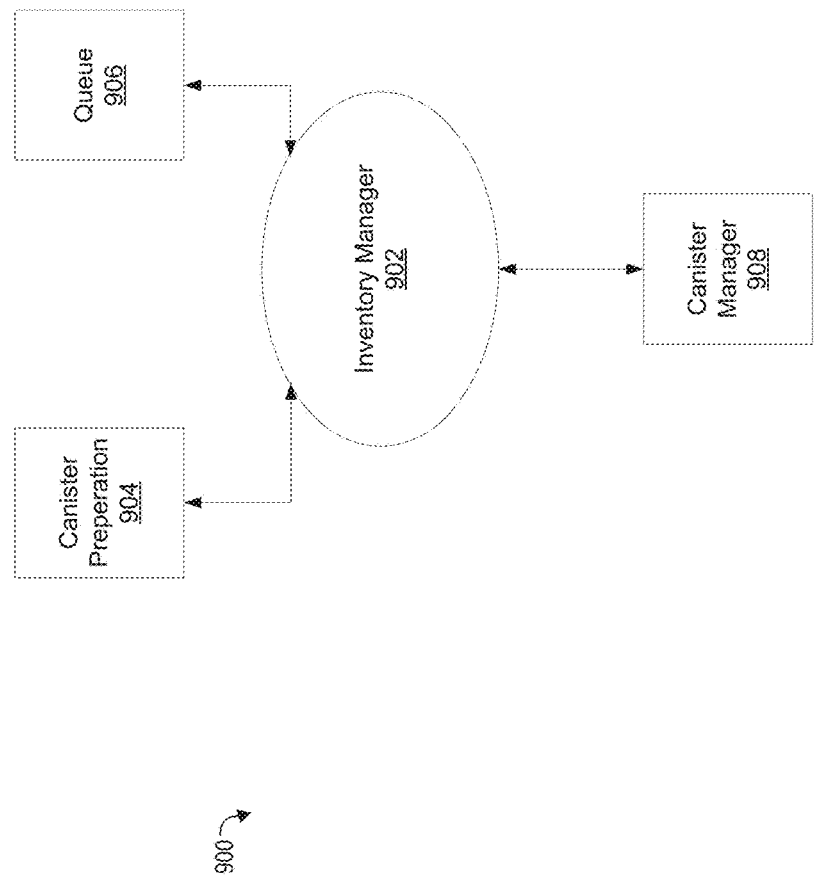

FIG. 9 is a block diagram of operation of an inventory manager 902, according to one embodiment. Canister preparation module 904 can receive data for each canister from the refill device, i.e., as each canister is being prepared (i.e., refilled or filled for a first time) by the refill device. Inventory manager 902 receives data from a canister preparation module 904 and from queue manager 906 to determine whether the pill inventory (i.e., in the canister) matches the pack data that is queued up in queue. Inventory manager 902 communicates the results of this analysis to canister manager 908 and/or queue manager 906.

Figure 10:
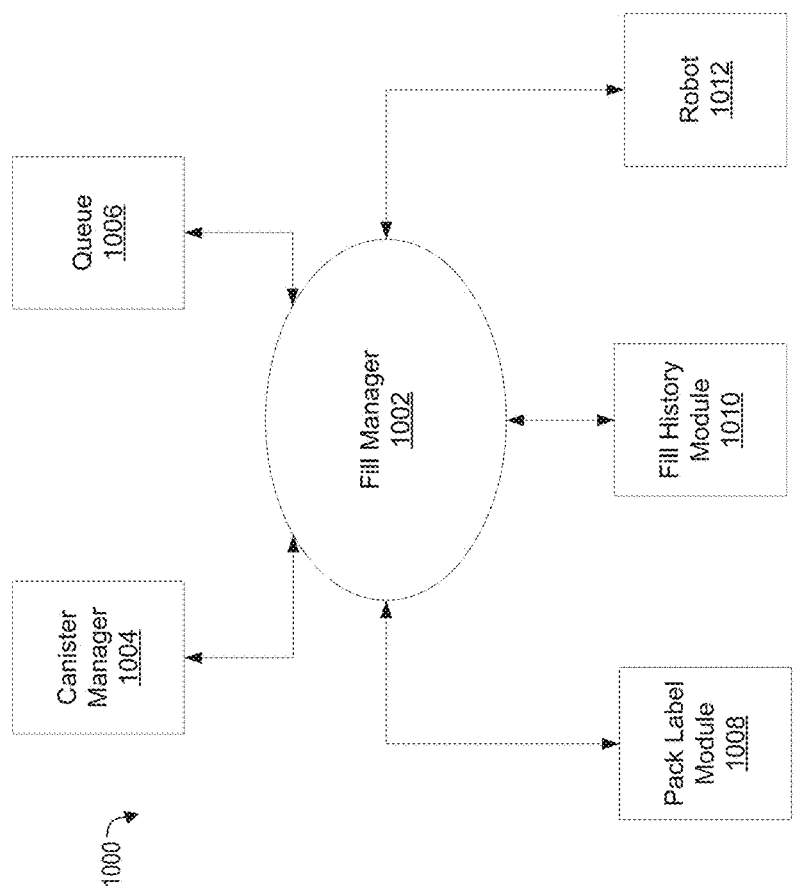

FIG. 10 is a block diagram of operation of a fill manager 1002, according to one or more embodiments. Fill manager 1002 communicates with a canister module 1004, a queue 1006, a pack label module 1008, a fill history module 1010, and a robot 1012.

Fill manager 1002 is configured to receive data from canister module 1004. This data can indicate what types of pills are used, how many pills of each type are left in the canister, how many pills are used from an exception tray, and the like. Fill manager 1002 also receives data from queue 1006. This data can indicate the amount of pill pack data that is queued in queue 1006.

Fill manager 1002 communicates data to pack label module 1008. This data can indicate what label to place on each pill pack that is generated by the robot. Fill manager 1002 communicates data to fill history module 1010. This data can indicate to fill history module 1010 to log the fill history, i.e., the amount, type, date and time used, etc., of the pills stored, the pills used when making pill packs, and types of pill plans that are processed. Fill manager 1002 also communicates data to robot 1012. This data can indicate any of the data that is sent to pack label module 1008 and fill history 1010. This data can also indicate when pack label module 1008 will generate and/or affix a label on each pill pack. Robot 1012 can implement pill dispensing robot 100 of FIG. 1. Robot 1012 can be implemented by robot controller 762, and be configured to control various motors, sensors, trapdoors, etc., for operation of the pill dispensing robot.

Figure 11:
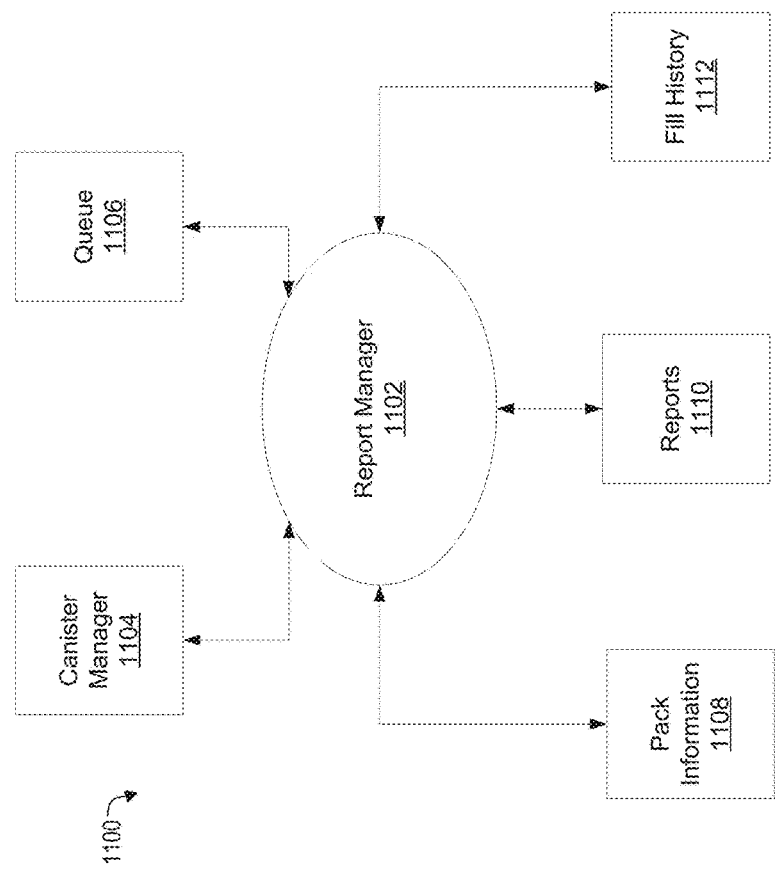

FIG. 11 is a block diagram of operation of a report manager 1102, according to one or more embodiments. Report manager 1102 communicates with a canister module 1104, a queue 1106. Report manager can generate pack information 1108, one or more reports 1110, and communicate with a fill history module 1112.

Report manager 1102 is configured to receive data from canister manager 1104. This data can indicate what types of pills are used, how many pills of each type are left in the canister, how many pills are used from an exception tray, and the like. Report manager 1006 also receives data from queue 1106. This data can indicate the amount of pill pack data that is queued in queue 1106. Report manager 1102 generates reports 1110 that based on analyzed information from canister module 1104 and queue 1106. As noted below, queue 1106 can include a to-be-scheduled queue, a to-be-performed queue, and a wait queue, beside others.

Figure 12:
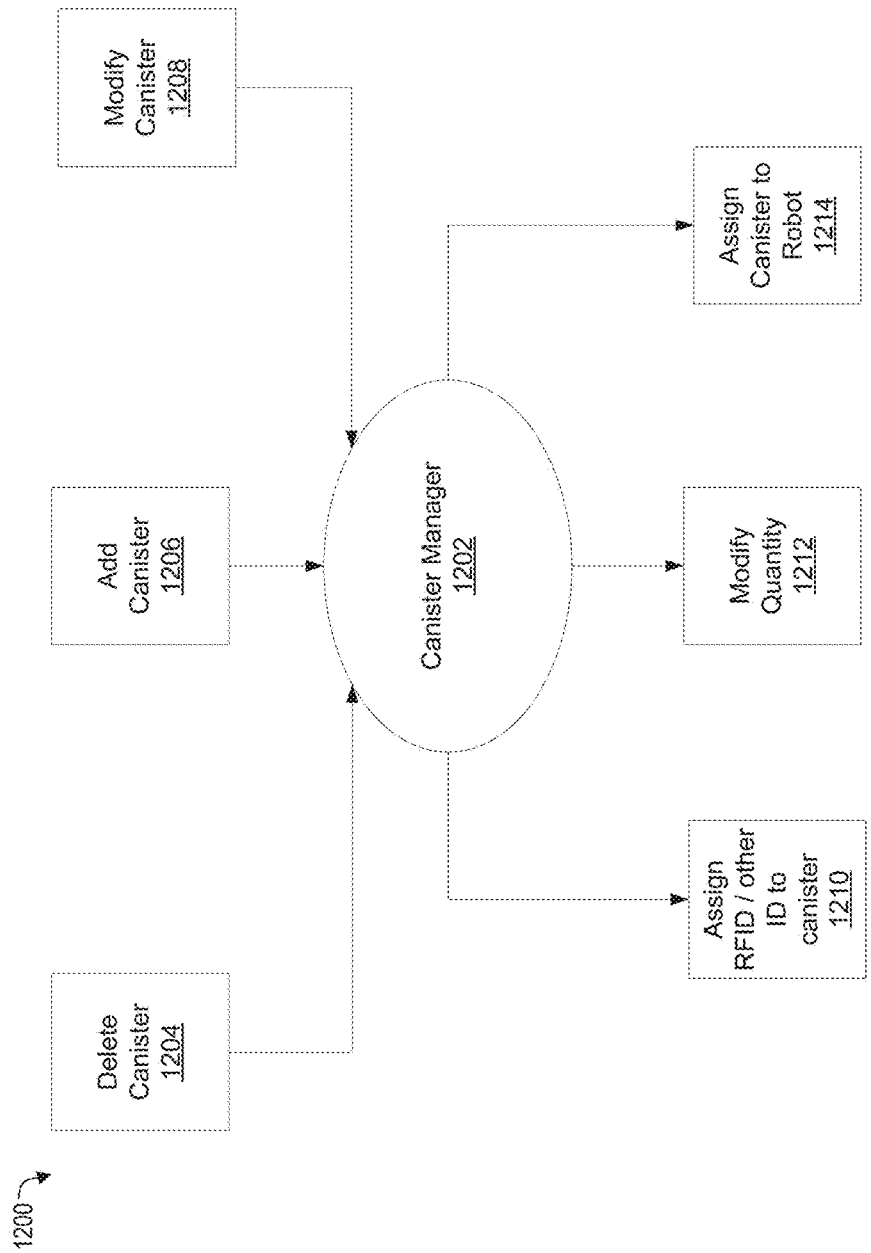

FIG. 12 is a block diagram of operation of a canister module 1202, according to one or more embodiments. Canister manager 1202 communicates with other modules, such as an inventory manager, a queue manager, a fill manager, a report manager, and/or a robot controller. One or more of these modules can send various commands to canister manager 1202. Furthermore, canister manager 1202 can send other commands and/or data to these other modules. In one embodiment, canister manager 1202 communicates with a refill device, such as illustrated by FIG. 2E. Canister manager 1202 can receive data for each canister from the refill device, i.e., as each canister is being prepared (i.e., refilled or filled for a first time) by the refill device.

Canister manager 1202 can receive commands to delete a canister 1204, add a canister 1206, or to modify a canister 1208. These commands can be received from any of the above listed modules. In one embodiment, these commands are generated automatically, i.e., by the sensor assembly of the container module (such as the container module of FIG. 8), where when a canister is placed (i.e., added) or deleted, or contents of a canister are somehow modified (i.e., different pills are placed along with a new identifying RFID tag), these commands are send from the container module to canister module 1202. Canister module 1202 then registers the change in the containers. Canister manager 1202 can generate commands to assign RFID (or another ID) to a canister 1210, to modify quantity of canisters (or pills in each canister) 1212, or to assign a canister to a robot 1214.

During the registering process, when canister module 1202 assigns 1210 RFID and/or another ID to canister, this new canister is registered within the control module framework. At this point, the scheduler, inventory manager, and other modules account for the pills and location of this canister. When pills are added to a canister (such as via a refill device), this refill device can communicate a modified 1212 pill quantity, which is processed by canister manager 1202. The pill quantity can be modified, for example, by the inventory manager. Furthermore, during the registering process, canister module 1202 assigns 1214 canister to the robot. Once the canister is assigned, the new canister can be implemented by the control module when dispensing pills according to a current plan.

Figure 13:
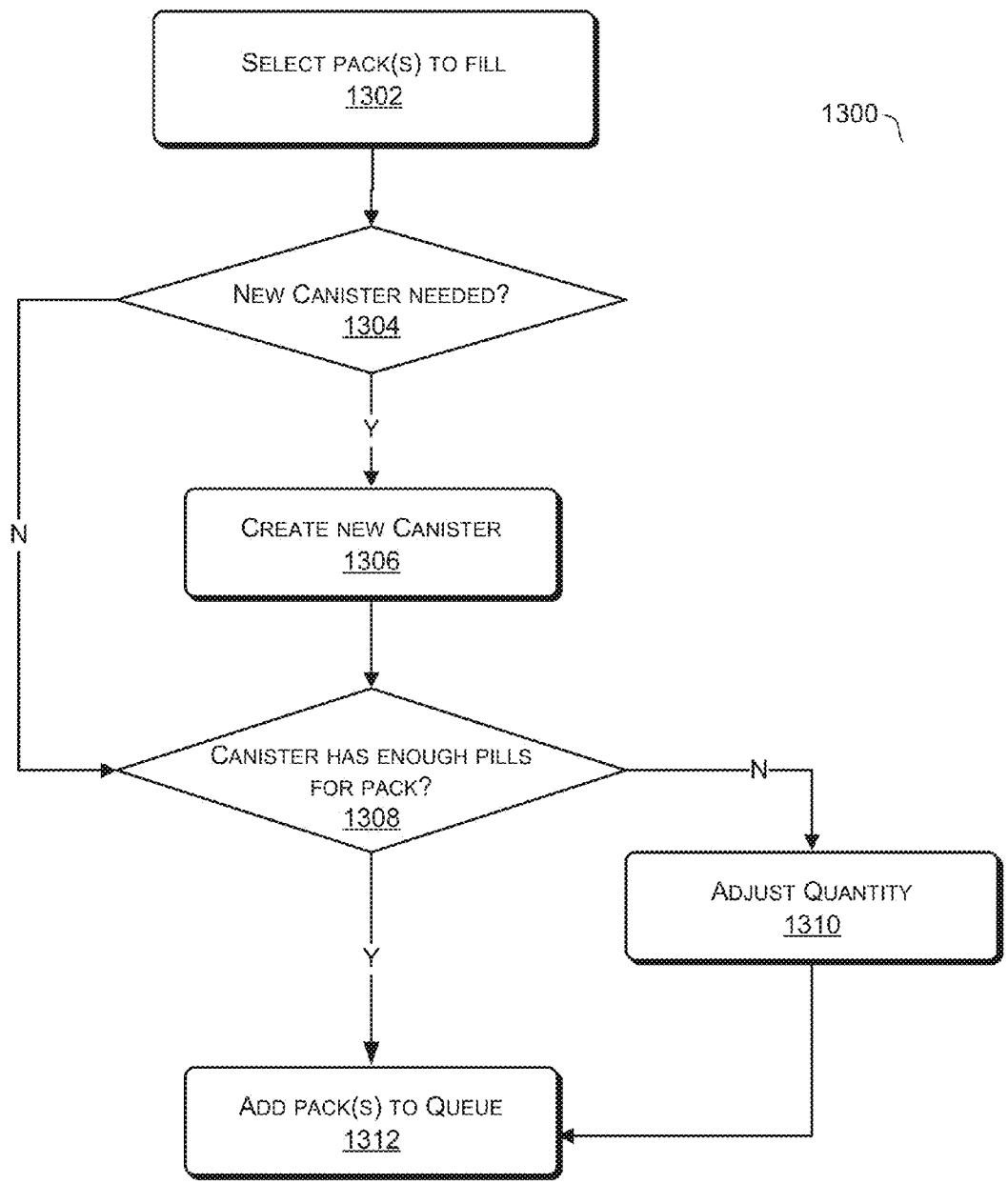
FIG. 13 is a flowchart of a method of using canisters by the pill dispensing robot, according to some embodiments.

FIG. 13 is a flowchart illustrating a method 1300 of operation of a control module, according to one or more embodiments. It is noted that the flowchart of FIG. 13 can be performed by one or more modules that access robot 100. Furthermore, this method may be modified in order to derive alternative embodiments. Also, the steps in this embodiment are shown in sequential order. However, certain steps may occur in a different order than shown, certain steps may be performed concurrently, certain steps may be combined with other steps, and certain steps may be absent in another embodiment. Method 1300 is described with reference to variations of the elements described in connection with FIGS. 1-12. In one implementation, method 1300 is performed by a canister module, such as canister module 1202.

In one implementation, method 1300 is performed to determine whether the next pill pack that is accessed can be placed into the queue (that is processed by the control module). Once the control module determines that a pill pack can be created according to the pill pack data, that pill pack data is placed in (i.e., stored using) a to-be-completed queue (or another memory location), as described below.

In element 1302, the control module selects one or more pill packs to fill. The control module can select such pill pack data from a to-be-scheduled queue, or from another memory location that stores data for pill packs that have not yet been placed in the to-be completed queue.

In element 1304, the control module determines whether a canister is needed. The control module determines (such as by communicating with the inventory manager) whether the current canisters (i.e., at the time of performing element 1304) contain the appropriate type and amount of pills for this pill pack data. If a new canister is needed, element 1306 is performed. If a new canister is not needed, element 1308 is performed.

In element 1306, the control module creates data (e.g., creates a new data entry and populates it with certain characteristics) associated with a new (physical) canister. The control module can create a new canister by requesting that a new canister be added (e.g., with a certain type and/or amount of pills). This request can be indicated to a user, such as via a GUI. In one implementation, the control module can select a new physical canister to be installed, such as from a canister repository. The control module thus creates and associated canister data for a new physical canister.

In element 1308, the control module determines whether the canister has enough pills to fulfill the pill requirements of the pill pack being currently processed. The control module thus determined that a container having the appropriate type of pills is present in the canister module. However, this canister may not contain an appropriate amount of pills. If the canister has enough pills, element 1312 is performed. If the canister does not have enough pills, element 1310 is performed.

In element 1310, the control module adjusts quantity of the pills that will be dispensed. In one implementation, the control module can indicate, such as using a GUI (and/or an LED on the canister, the extra pill tray, and/or via other means) that additional pills are needed (i.e., of the type already present). Once the canister module receives additional pills, the control module updates the current pill quantity for that canister (or for the extra tray if used instead).

In element 1312, the control module adds the pack data to the queue. The control module thus determines that the container module includes the proper type and amount of pills that are needed to fill a pill pack using the pill pack data.

If the canisters, the substitutions pills, or the exception tray do not have the pills required for the pill pack, the pill pack data is not added to the queue of the pill packs to be fulfilled, and it is instead placed in a wait queue (or another memory location). The wait queue contains pill pack data that cannot be processed by the control module. The control module checks, such as by accessing the inventory manager, whether the current inventory has the required number and/or type of pills to fulfill the pill pack. These checks can be performed periodically (e.g., such as on a predetermined or a dynamically adjusted interval), and/or in response to the canister module registering a canister change event. The canister change even can also indicate a canister addition, deletion, or modification. In one implementation, the system allows the user to add a pack to the queue even if that pack requires pills that are not present at the time of the pack addition; the inventory system can rectify this shortcoming in various ways, as described herein.

It is noted that the methods of FIGS. 14 and 16-20 may be modified in order to derive alternative embodiments. Also, the steps in these embodiments are shown in sequential order. However, certain steps may occur in a different order than shown, certain steps may be performed concurrently, certain steps may be combined with other steps, and certain steps may be absent in another embodiment. Methods 1400 and 1600-2000 are described with reference to variations of the elements described in connection with the previous Figures.

Figure 14:
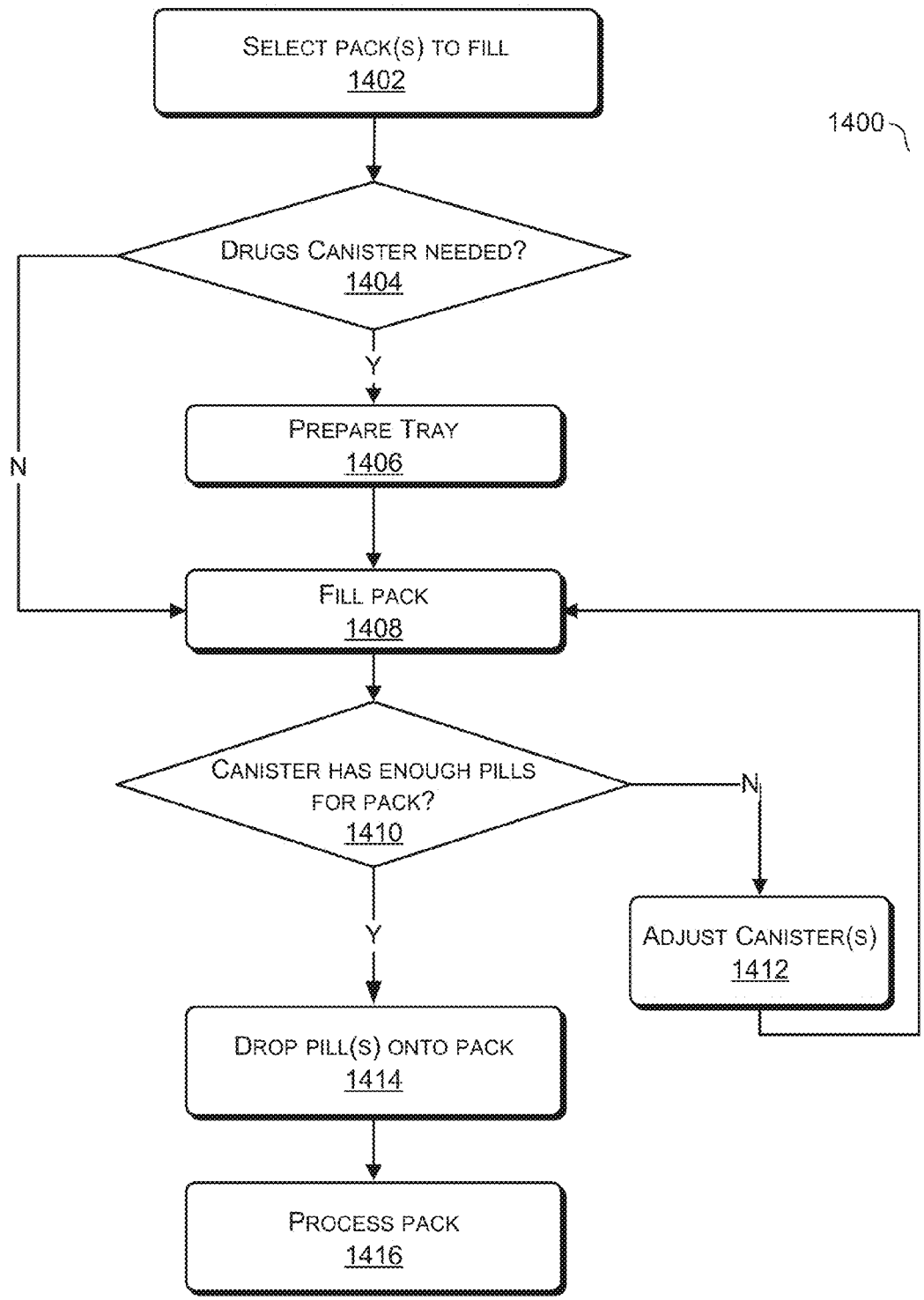
FIG. 14 is a flowchart of a method of processing pill packs by the pill dispensing robot, according to some embodiments.

FIG. 14 is a flowchart illustrating a method 1400 of operation of a control module, according to one or more embodiments. In one implementation, method 1400 is performed as a part of processing pill pack data. Thus, method 1400 can be performed by a robot control module. Once the control module determines that a pill pack can be created according to the pill pack data, that pill pack data is placed in a to-be-completed queue, as described below.

In element 1402, the control module selects one or more pill packs to fill. In element 1404, the control module determines whether another drug canister and/or a use of an exception tray (i.e., to receive manually placed pills) is needed. This determination can be based, for example, if the plan contains a pill of a type that is not currently available in the present containers.

If the drug canister is needed, element 1406 is performed. If the drugs canister is not needed, element 1408 is performed. In element 1408, the control module fills the pill pack. In element 1410, the control module determines whether the canister has enough pills to prepare the pill pack according to the pack data. If the canister does not have enough pills, element 1412 is performed. If the canister has enough pills, element 1412 is performed. It is noted that although the control module already checks whether or not the canister module has enough pills prior to performing method 1400, for various reasons (such as a miscount of pills, the pills not being processed properly and being taken out, a canister being replaced with another canister, and the like), when processing a certain pill pack data, the actual type and/or amount of pills in a container may be different from that previously calculated.

In element 1412, the control module adjusts the canister, such as by adjusting the number of pills in the canister. The control module can prompt the user to add more pills using the refill device, for example. In element 1414, the control module drops one or more pills onto a pack, such as described with reference to FIG. 1C.

In element 1416, the control module processes the pack. The pack processing can involve verifying whether the amount and/or type of pills in each entry of the pill pack corresponds to the pill pack data, sealing the pill pack once the verification is complete, affixing a label onto the sealed pill pack, and/or moving a transport element to position a next pill pack to receive pills according to a next pill pack data in the queue.

Figure 15:
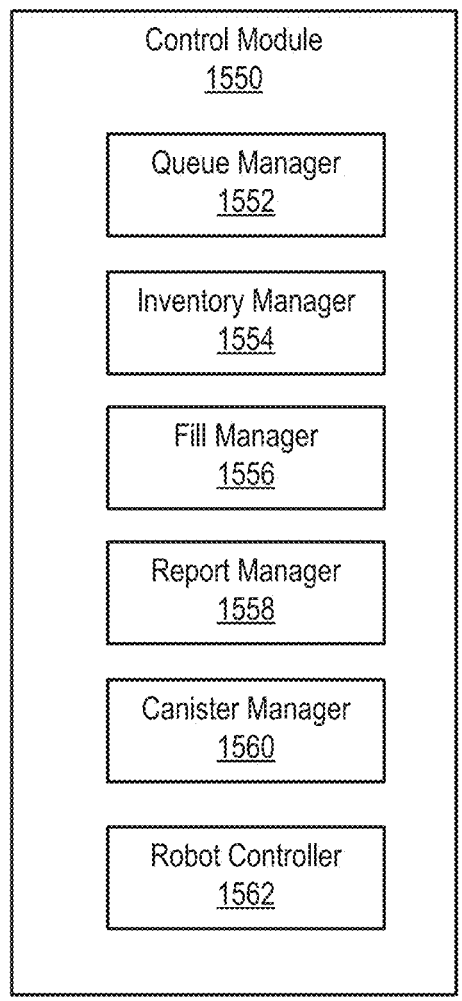
FIG. 15 is a block diagram of a control module of a pill dispensing robot, according to some embodiments.

FIG. 15 is a block diagram of a control module 1550, according to one embodiment. Control module 1550 includes a queue manager 1552, an inventory manager 1554, a file manager 1556, a report manager 1556 (which can implement a report module), a calendar manager 1560, and a robot controller 1562. Various ones of these modules are described herein with reference to the other figures. Modules of FIG. 15 can be implemented using software, hardware, and/or a combination thereof. For example, modules of FIG. 15 can be stored using memory (such as RAM, flash memory, and the like, as also described in other figures) and executed using one or more processors. Furthermore, it is understood that although FIG. 15 illustrates various modules of control module 1550 as being stored using one memory element, in some implementations these modules can be distributed across several computing devices, e.g., each being stored in a separate memory and executed by separate processor(s), respectively.

It is noted that robot controller 1562 controls the operation of the robot. Furthermore, control module 1550 also receives various signals, indications, messages, and the like, regarding the operation and/or current status of the robot, including the status of the pill container, the location of the pill pack (e.g., on a rotating table or on a moving belt), and the like. In other words, control module 1550 can both send data, indications, and/or commands to other modules, as well as receive data/commands/indications from other modules.

Figure 16:
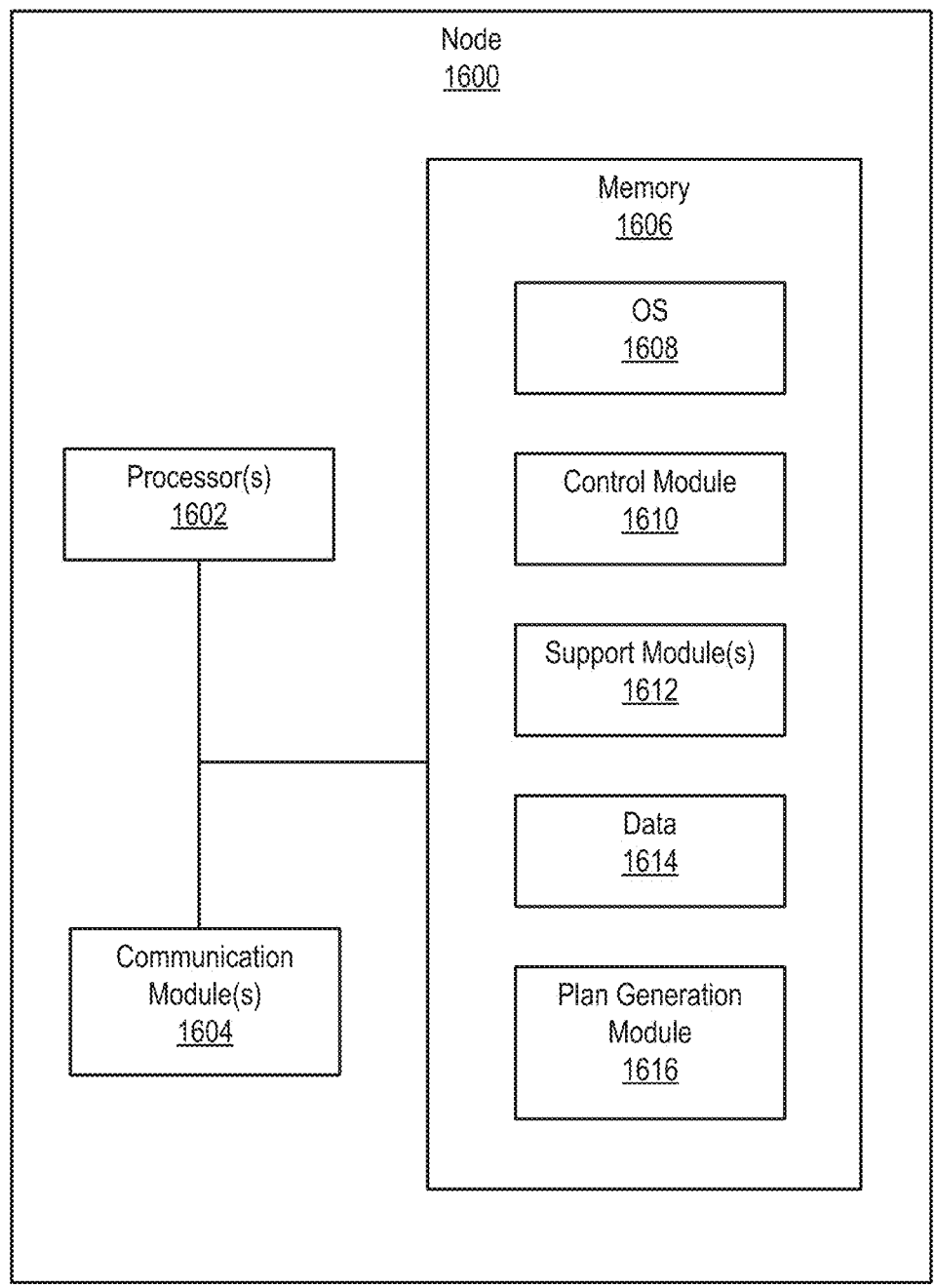
FIG. 16 is a block diagram of a node that can implement the control module of the pill dispensing robot, according to some embodiments.

FIG. 16 is a block diagram of a node 1600 that can implement the computing devices of FIG. 1, according to one or more embodiments. Node 1600 includes one or more processor(s) 1602, a communication subsystem 1604, and memory 1606. Memory 1606 can include one or more of operating system 1608, control module 1610, support modules 1612, data 1614, and plan generation module 1614. Processor(s) 1604 can execute one or more of operating system, control module 1610, and/or manager module 1614. Control module 1610 can implement the control modules of the previous Figures, and can implement one or more of methods 160, 600, 1400, as well as the functionality shown in FIGS. 7-12. Communication subsystem 1604 can facilitate communication with other nodes over a network. Plan generation module 1616 can implement the control modules of the previous Figures, and can implement one or more of methods 150 and 1700-2100. Data 1612 can implement data used by these various modules. It is noted that in some embodiments, one or more of elements of node 1600 may not be used. In some embodiments, one or more of elements of node 1600 may be combined, as desired.

Plan Generation Module

Figure 17:
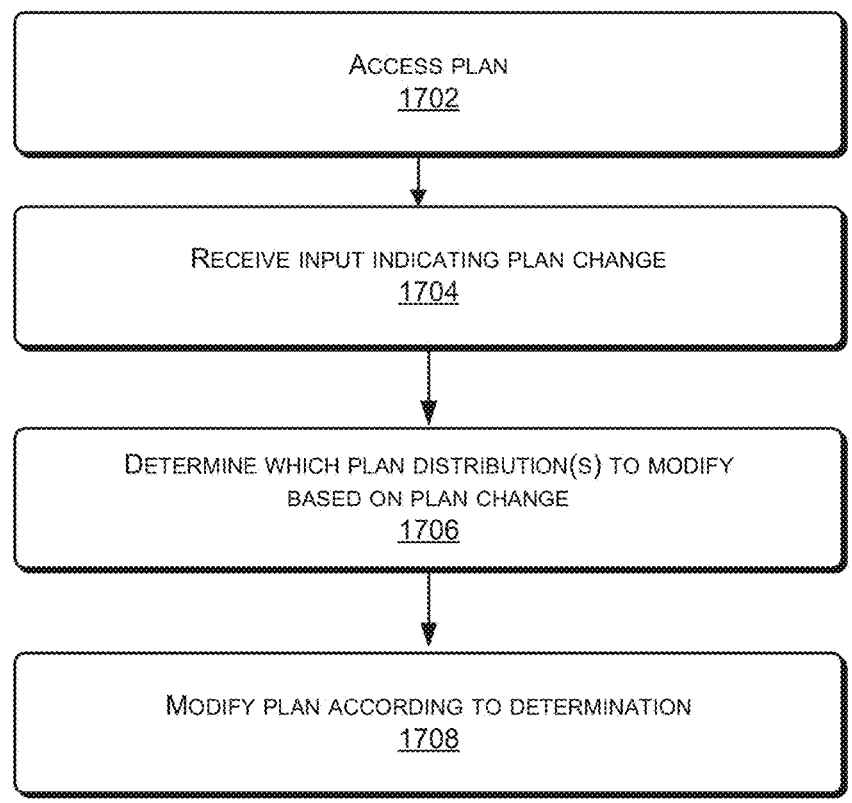
FIG. 17 is a flowchart of a method for modifying a plan for by a plan generation module, according to some embodiments.

FIG. 17 is a flowchart illustrating a method 1700 of modifying a pill plan by a plan generation module, according to one or more embodiments. It is noted that method 1700 can be also performed by the robot's control module. In one implementation, method 1700 is performed as a part of modifying pill pack data. The modified pill pack data is then communicated to the robot's control module, where it is processed and/or queued, as described above.

In element 1702, the plan generation module accesses a plan. The plan can be implemented as a single or multiple pill pack data. In one implementation, the plan includes pill pack data and additional metadata associated with the pill pack data. The pill pack data can specify the type, amount, Hours of Administration (HOA), whether a generic/substitute drug can be used instead of a certain drug, priority of that pill pack, a certain time by which that pill pack needs to be processed, and the like. The pill pack data can be formatted using a variety of digital formats. It is noted that if the user receives new prescriptions for a new patient, the plan generation module can use a template to generate the pill plan, such as described below with reference to FIG. 18.

In element 1704, the plan generation module receives inputs indicating plan change. The plan generation module can receive inputs from a variety of sources, such as another program (i.e., via commands/instructions/notifications), from one or more files, from a user (such as via a GUI or another type of a user interface), and the like.

In element 1706, the plan generation module determines which plan distribution to modify based on the plan change. For example, depending on the HOAs of the current plan, the plan generation module can determine to modify the distribution of a second day to include pill distribution of a first day in situations where the distribution for a first day is full, but the distribution for the second day has available time slots. This is further explained with relation to the Figures below.

In element 1708, the plan generation module modifies the plan according to the determination of element 1706. The modified plan can then be sent to the robot, e.g., to the control module, for processing.

Figure 18:
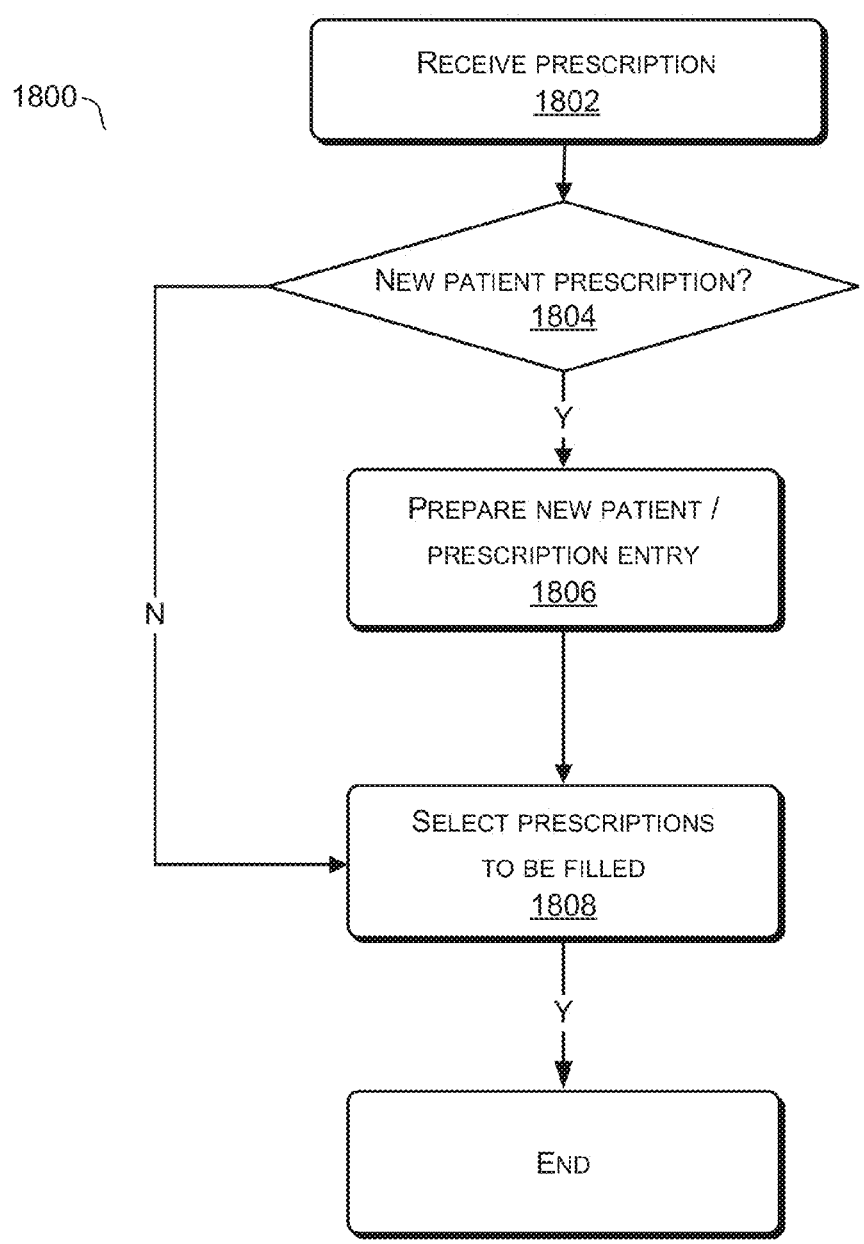
FIG. 18 is a flowchart of a method for processing templates, according to some embodiments.

FIG. 18 is a flowchart illustrating a method 1800 of selecting prescriptions, according to one or more embodiments. It is noted that method 1800 can be also performed by the robot's control module. In one implementation, method 1800 is performed by plan generation module 124. In one implementation, method 1800 is performed prior to selecting or accessing pill pack data.

In element 1802, the plan generation module receives a prescription. The prescription can specify one or more pills to be distributed (i.e., to a patient) at certain times and for a certain amount of time. The prescription is typically associated with a certain patient.

In element 1804, the plan generation module determines whether the prescription is a new patient prescription or an existing patient prescription. The plan generation module can access, for example, a database of existing patients and/or prescriptions to check the received prescription against the existing data. If the plan generation module determines that the prescription is a new patient prescription, element 1806 is performed. Otherwise, element 1808 is performed.

In element 1806, the plan generation module prepares a new patient and/or new prescription entry. If the received prescription is for a new patient, then both a new patient data and associated new prescription data are generated. Otherwise, if there's a match for a patient, the received prescription is associated with the existing patient.

New patient data can contain data that characterizes the patient, including identification characteristics (e.g., name, age, sex, date of birth, address, known drug allergies, etc.). The patient data can be associated with prescription data, as well as with pill pack data.

In element 1808, the plan generation module selects one or more prescriptions to be filled. The prescription is filled, for example, by adding it to certain pill pack data. In other words, the prescription, once selected, then can be added to an existing pill pack data (i.e., for an existing patient), or a new pill pack data can be generated for a new patient. For example, an addition of a prescription to an existing pill pack distribution can redistribute the distribution of HOAs of the pills.

Figure 19:
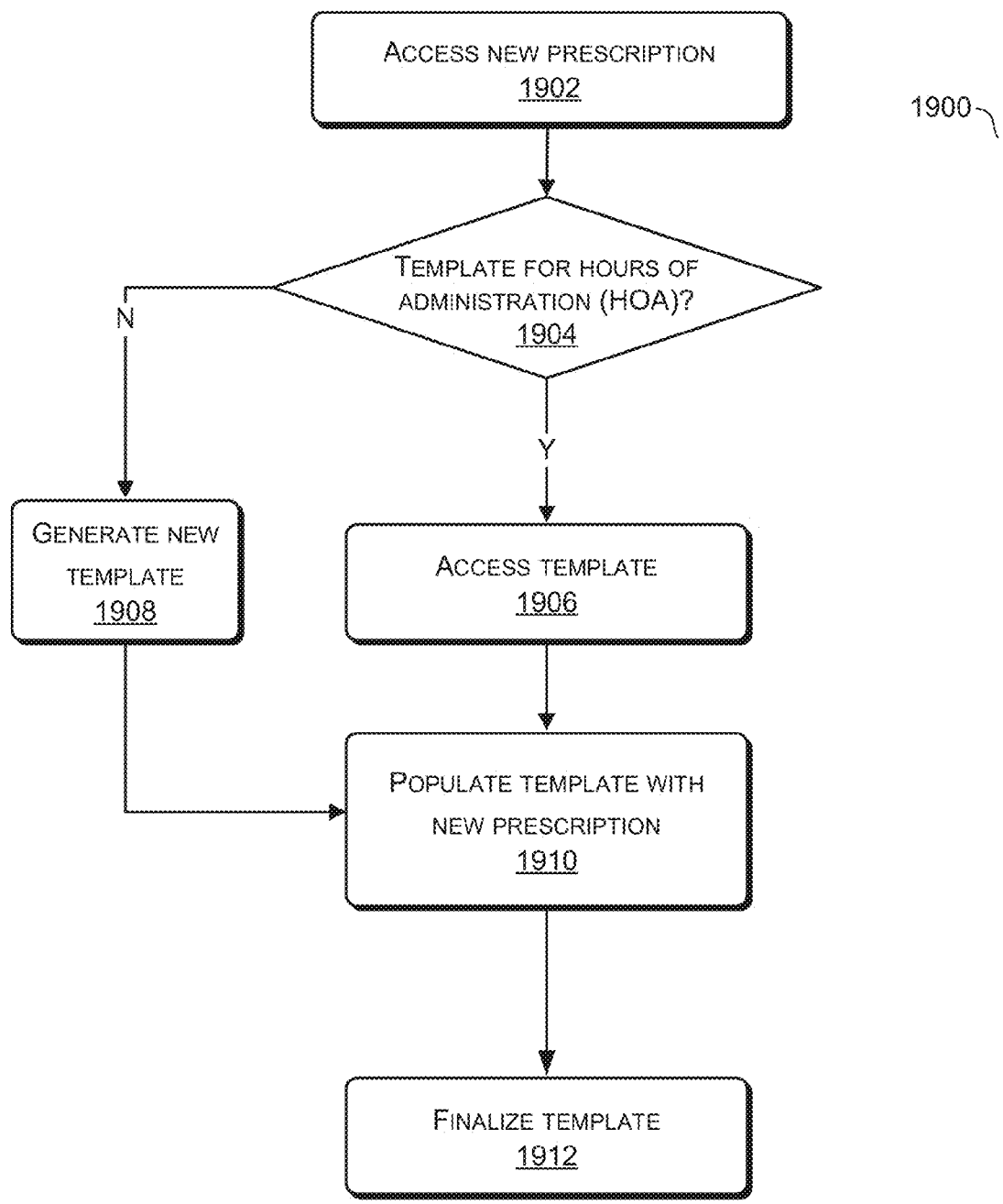
FIG. 19 is a flowchart of a method for processing prescriptions, according to some embodiments.

FIG. 19 is a flowchart illustrating a method 1900 of selecting prescriptions, according to one or more embodiments. It is noted that method 1900 can be also performed by the robot's control module. In one implementation, method 1900 is performed by plan generation module 124. In one implementation, method 1900 is performed as part of generating a new pill pack data, such as for a new patient and/or a new pill pack data for an existing patient.

In element 1902, the plan generation module accesses a new prescription. The prescription specifies a distribution of a certain pill type. The prescription is typically associated with a patient.

In element 1904, the plan generation module determines whether there's an existing template that can be associated with the prescription. The association can be made, for example, if the HOA of the template matches with the HOA of the prescription. For example, there may be some templates that have two HOAs per day, and some templates that have five HOAs per day. It is noted that the eventual pill pack would also have enough rows and columns to match with the HOA of the template. If the plan generation module determines that the template exists, element 1906 is performed. Otherwise, element 1908 is performed.

A template typically indicates the slot for each drug it associated hours of administration (HOA). A template is based on patient ID and the packing type ID. Drug details of the template include drug's Clinical Formulation ID (CFI), Hours of Administration (HOA), slot number, and/or number of pills to be taken for each slot, and the like. In one implementation, the plan generation module uses CFI as the basis for each drug, meaning that if a doctor decides to change the drug/NDC (i.e., and thus changing the prescription), but if the new drug/NDC has the same CFI, the plan generation module does not modify the template. In one implementation, the template information is based on a 7-day supply, but other supply approaches can be used instead.

A one week pill pack (also referred to as a bubble pack) typically has four columns representing Morning, Noon, Evening, Bed (MNEB) dose times (that correspond to the HOAs of the drugs), such as shown by FIG. 23. Morning time range is typically 6:00 to 10:59 AM, noon time range is typically 11:00 AM to 3:59 PM, evening time range is typically 4:00 to 6:59 PM and bed time range is typically 7:00 to 11:59 PM (or even until 5:59 the next day, depending on the implementation.

In element 1906, the plan generation module accesses the template. In element 1908, the plan generation module generates a new template. The new template includes the number of HOAs that correspond to the prescription. In one implementation, the plan generation module determines whether there are additional prescriptions associated with the patient prior to generating a new template.

In element 1910, the template (an existing template or a new template) is populated with the new template. In element 1912, the template is finalized, which can include template modifications. Finalization of the template can include verifying that the template can be processed by the robot control module. These techniques are described in more detail below.

Figure 20:
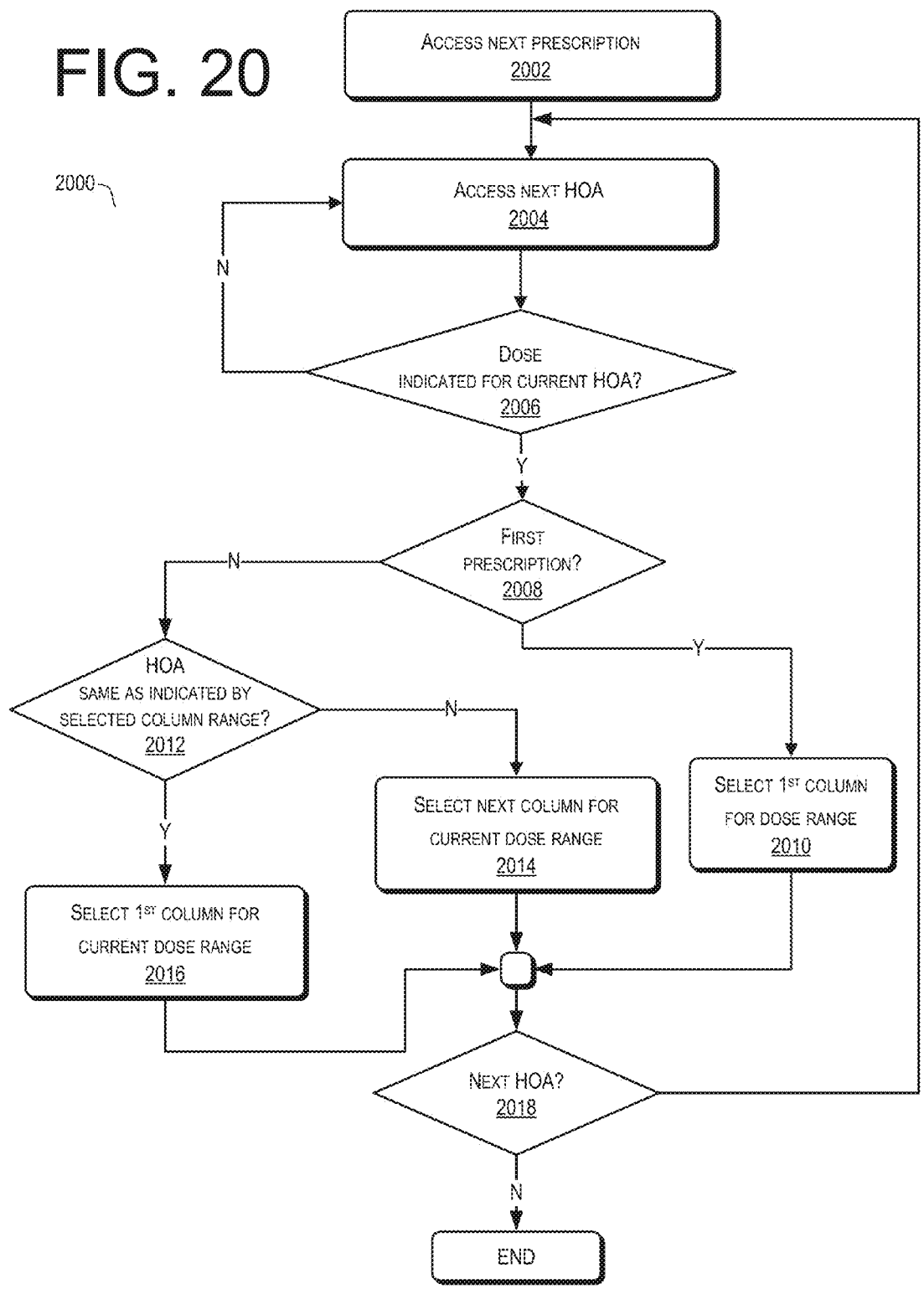
FIG. 20 is a flowchart of a method for modifying a template based on prescriptions, according to some embodiments.

FIG. 20 is a flowchart illustrating a method 2100 of a template generation, according to one or more embodiments. It is noted that method 2000 can be also performed by the robot's control module. In one implementation, method 2000 is performed by plan generation module 124. In one implementation, method 2000 is performed as part of generating a new pill pack data, such as for a new patient and/or a new pill pack data for an existing patient.

In element 2002, the plan generation module accesses a new prescription. As noted above, the prescription specifies a distribution of a certain pill type, for a certain patient. The plan generation module can access multiple prescriptions, one at a time. The plan generation module uses the HOAs indicated by the multiple prescriptions to generate a pill plan. For example, a pill plan for a given patient can include pill distributions indicated by several different prescriptions. Put another way, the plan generation module generates pill pack data that is used by the robot to make a pill pack for a given patient.

In element 2004, the plan generation module accesses the next HOA of the currently chosen prescription. If element 2004 is performed for a first time for a given prescription, then the plan generation module accesses a first HOA of that prescription. If element 2004 is performed for a second or a subsequent time for a given prescription, then the plan generation module accesses a corresponding second or a subsequent HOA for that prescription. For example, if element 2004 is performed for a third time for a given prescription, then the plan generation module would access the third HOA (such as an evening HOA) for that prescription.

In element 2006, the plan generation module determines whether there's a dose indicated for the current HOA. For example, the plan generation module can determine whether there's a dose for a morning HOA (e.g., 6 am to 10:59 AM). Upon a next execution of element 2004, the plan generation module can determine whether there's a dose for a noon HOA (e.g., 11 am to 3:59 PM). The next executions of element 2004 would include the plan generation module determining whether there are doses for evening HOA (e.g., 4 PM to 6:59 pm) and night HOA (e.g., 7 PM to 3:59 am of the next day), respectively. If the plan generation module determines that there's a dose for a current HOA, element 2008 is performed. Otherwise, element 2004 is performed.

In element 2008, the plan generation module determines whether the current prescription is a first prescription used for a given (pill pack data) template. If the plan generation module determines that the current prescription is the first prescription, element 2010 is performed. Otherwise, element 2012 is performed.

In element 2010, the plan generation module selects a first column for the dose range. The dose range is indicated by the HOA. For example, if the first column corresponds to pill distributions for morning HOA, the plan generation module can select pill distributions for this column.

In element 2012, the plan generation module determines whether the current HOA is the same as indicated by a selected column range. In one implementation, the selected column range is the first column range for the given HOA. Each column can initially indicate a different day. For example, a first column of the template can indicate a first time-of-day, a second column of the template can indicate a second time-of-day, and so forth. In another implementation, another correlation between HOAs and columns can be used.

In element 2014, the plan generation module selects a next column for the current dose range. For example, if the first column corresponds to pill distributions for a morning HOA, the plan generation module can select pill distributions for a second column that is associated with a noon HOA (such as shown in an example pill pack of FIG. 23).

In one implementation, in element 2014, the plan generation module determines whether the current dose range should be split into another pill pack. This determination is made if the number of pills for a given HOA (e.g., morning) exceeds the number of pills that can fit on a single pill pack element (e.g., a Sunday morning). If the plan generation module determines that columns and/or rows of the pill pack cannot be merged, instructions to use another pill pack are generated (i.e., that would contain the excess pills for the HOA(s)). The plan generation module also generates appropriate labeling instructions for the label module (e.g., module 706).

In one implementation, in element 2014, the plan generation module determines that the current dose range can be administered using merged columns and/or rows. For example, if there is no evening HOA for the prescriptions for the given patient, then if another HOA (e.g., the bedtime HOA) requires more pill pack elements, the plan generation module will merge the evening column and the bedtime column into two bedtime columns (this having no space for pills administered in the evening, as there are none). This is shown by FIG. 23. The plan generation module also generates appropriate labeling instructions for the label module (e.g., module 706).

In element 2016, the plan generation module selects a first column for the current dose range. For example, if the first column corresponds to pill distributions for a morning HOA, the plan generation module can select pill distributions for this column. If there is another HOA (as determined by 2018), then element 2004 is performed next. Otherwise, method 2000 ends.

Figure 21:
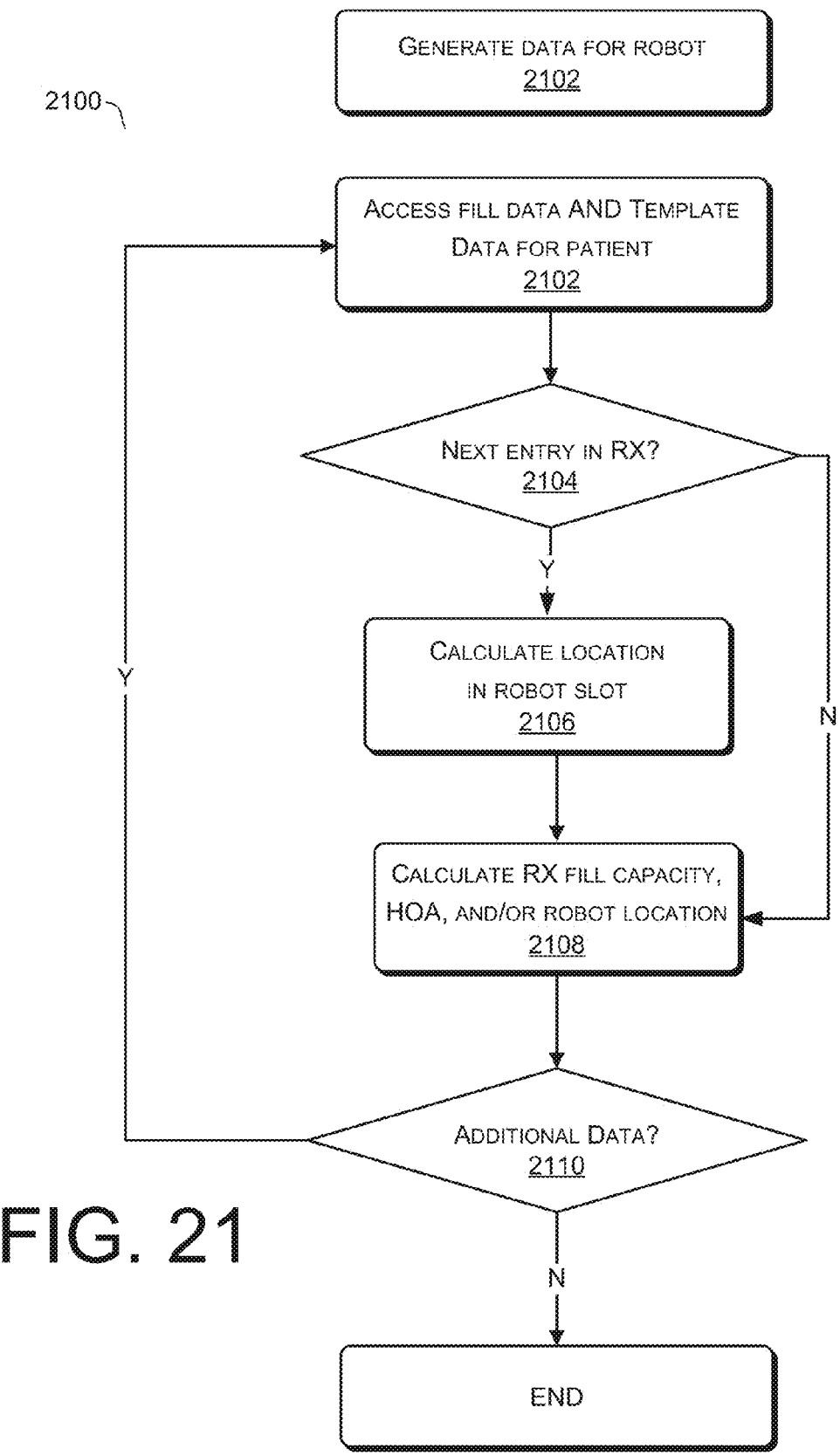
FIG. 21 is a flowchart of a method for generating data for a plan for the pill dispensing robot, according to some embodiments.

FIG. 21 is a flowchart illustrating a method 2100 of a generating pill pack data, according to one or more embodiments. It is noted that method 2100 can be also performed by the robot's control module. In one implementation, method 2100 is performed by plan generation module 124. In one implementation, method 2100 is performed as part of generating a new pill pack data, such as for a new patient and/or a new pill pack data for an existing patient.

In element 2102, the plan generation module accesses a template and a prescription. The prescription is selected by the plan generation module. The template is generated by the plan generation module, such as described above in FIG. 20.

In element 2104, the plan generation module accesses a next entry in the prescription. If element 2104 is performed for a first time, the plan generation module can access a first entry in the prescription. If element 2104 is performed a second or a subsequent time, the plan generation module accesses the next entry in the prescription (e.g., a second entry for a second performance of element 2104).

In element 2106, the plan generation module calculates a location in the pill pack where to drop the pills. When executing the plan, the robot drops the selected type and number of pills in the selected location of the pill pack (such as the pill pack of FIG. 23).

In element 2108, the plan generation module calculates prescription fill capacity and HOA. The fill capacity, the HOA, and the location in the pill pack are then stored using the pill pack data.

In element 2110, the plan generation module determines whether there's additional data in the prescription that can be mapped using the template to the pill pack data. If there's additional data, element 2104 is performed. Otherwise, method 2100 ends.

Figure 22A:
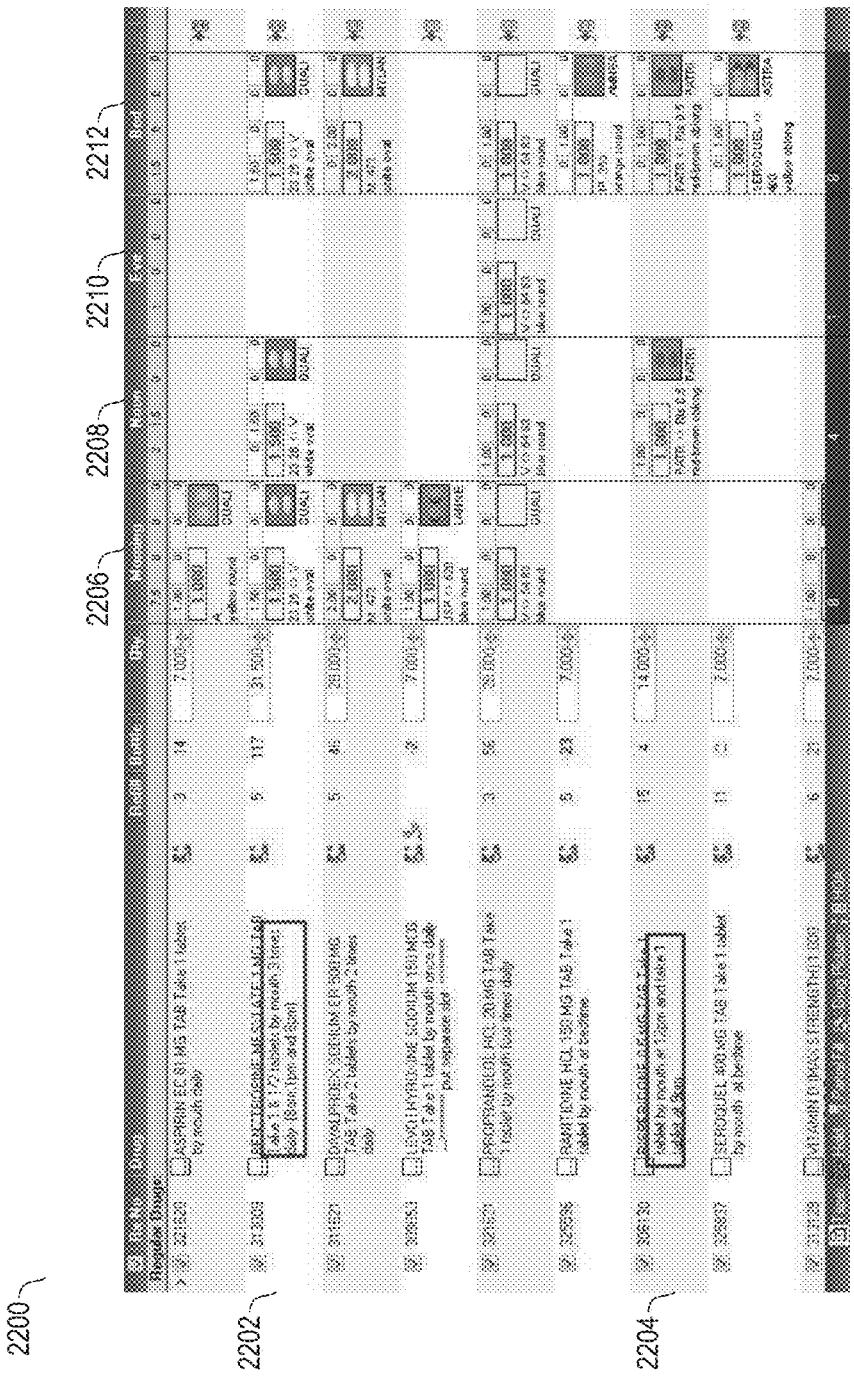
FIGS. 22A and 22B are block diagrams of template visualizations as used by the plan generation module, according to some embodiments.
Figure 22B:
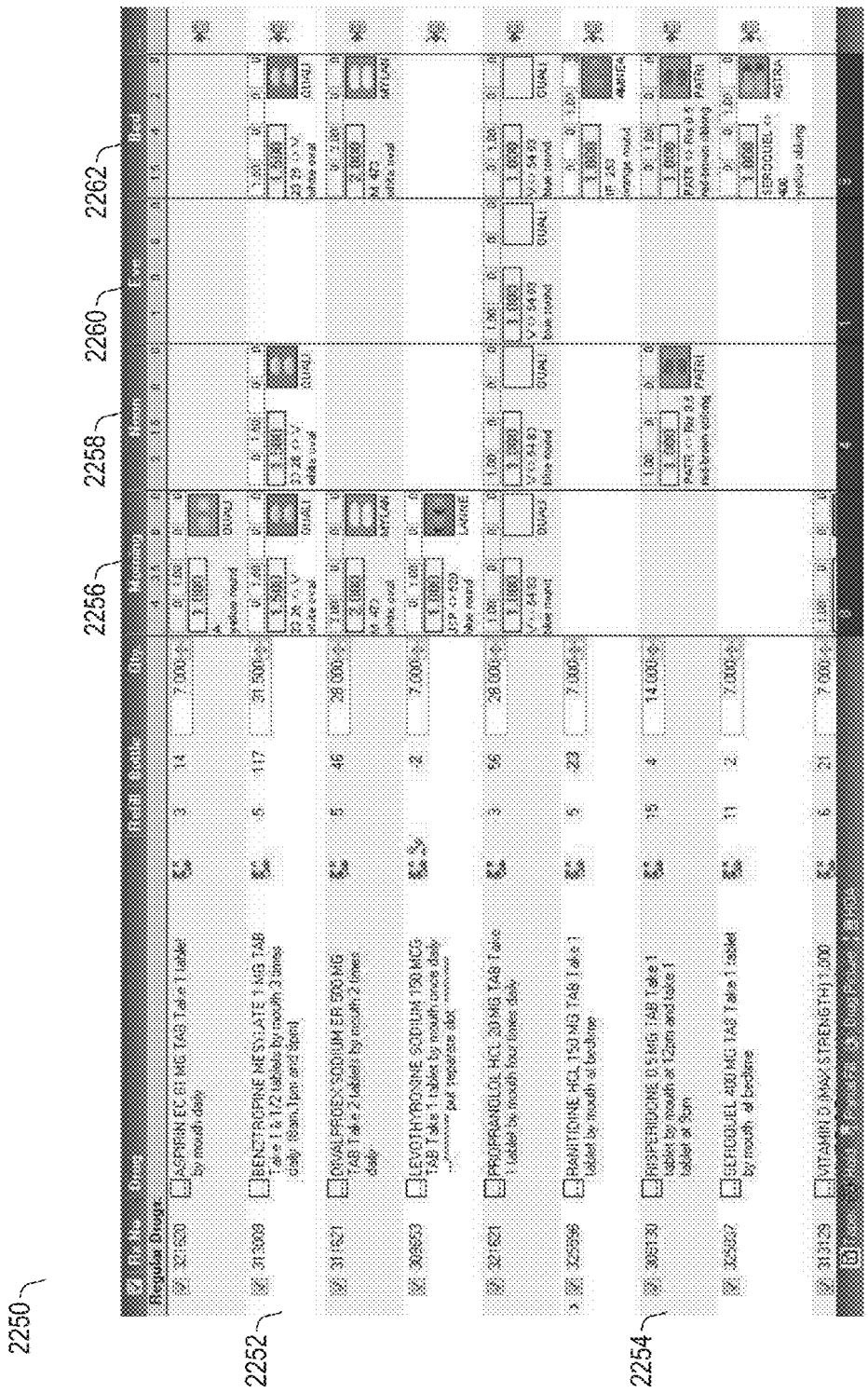

FIGS. 22A and 22B are block diagrams of template visualizations, according to some embodiments. Each such visualization can be presented, such as using a GUI, to a user of the plan generation module. The plan generation module can receive inputs, such as automatically generated internally and/or externally to the plan generation module, to modify each such template.

FIG. 22A illustrates a visualization 2200 of template that is suggested by the plan generation module, such as illustrated by FIG. 20. Template visualization 2200 includes several columns 2206-2212 which correspond to HOAs. In this example, there are four HOAs, morning 2206, afternoon 2208, evening 2210, and bedtime 2212, although the templates described herein can use of fewer or additional HOAs. Template visualization 2200 includes several rows, where each row corresponds to a separate prescription. Thus, each such template can indicate the HOAs for multiple prescriptions for a certain patient. As described above, the plan generation module generates pill pack data based on each such template.

It is noted that each column 2206-2212 includes four entries, which can correspond to the number of times each drug is given. In one implementation, each of these entries corresponds to a separate pill pack for the prescriptions grouped using the current template. Regardless of the number of pill packs used, it does not necessarily mean that the four columns of the pill pack are restricted to these four dose times (e.g., MNEB). Instead, the plan generation module can use the first two columns for drugs in the morning time range. So for this to be happen, each dose time is given a maximum of four dose times to split each dose time, considering that an actual pack has only four dose times. There are 16 slot numbers (as shown in FIGS. 22A and 22B), four each initially corresponds to the morning, noon, evening and bed doses. Slot numbers 1 to 4 correspond to morning, numbers 5 to 8 for noon, numbers 9 to 12 for evening and 13 to 16 for bed time.

In one implementation, FIG. 22A illustrates a template that is initially suggested by the plan generation module. In the example shown, the entire template fill is populated into two separate pill packs. A first pill pack holds all the drugs from Morning to Evening doses (one column for Morning, two for Noon and one for Evening making it a total of 4 columns). The second pill pack will hold all the drugs for Bed time doses.

The template can be retrieved by the plan generation module based on patient ID and packing type ID for a drug. Additional drug details can include drug's Clinical Formulation ID (CFI), HOA, slot number and number of pills to be taken. If the CFI, HOA and slot number combination for a given drug are not found in the system, the plan generation module can add one or more rows for these. If the CFI, HOA and slot number combination of the drug is found, the plan generation module can update the quantity. Any remaining CFI and HOA not in use will then be deleted from the template being used.

The plan generation module can modify the initially suggested template, such as based on guidelines and/or receiving user input (e.g., via a GUI). The template modifications can adjust the drug's pill size, hours of administration, and other considerations, which can adjust the placement of each drug on a particular dose time.

In this example, template visualization 2200 includes a second prescription 2202 that indicates a drug usage time of 1 pm for afternoon dose 2206, whereas a seventh prescription 2204 indicates a drug usage time of 12 pm for afternoon dose 2206. Furthermore, second prescription 2202 indicates a drug usage time of 8 pm for bedtime dose 2212, whereas seventh prescription 2204 indicates a drug usage time of 9 pm for bedtime dose 2212.

Furthermore, it is noted that the plan generation module (based on an analysis of the prescription, the current plan, etc.) can recommend that the HOAs for second prescription 2202 and for seventh prescription 22004 be split among two sub-columns of column 2208 (i.e., for afternoon dosage). As shown, each column includes four sub-columns. Each such sub-column can correspond to a separate pill pack that is generated by the robot, and thus to a separate pill pack that is given to the patient. In the example shown, there are two pill packs being generated, as indicated by non-zero numbers of each of the HOAs (such as 2 and 1.5 for afternoon HOA 2008).

If there is no template saved for this patient and packing type, then the plan generation module can create one based on the prescription data. As discussed above with reference to FIGS. 20 and 21, the plan generation module can loop through a list of prescriptions to be filled for a particular patient. If a prescription is marked for filling and is a regular prescription type, then the plan generation module can get all the HOA for this particular prescription (i.e., for the Rx).

Based on the HOA, the plan generation module determines the column of the template for that prescription. With reference to the template shown in FIG. 22A, if the administration time is a part of the Morning time range, then the plan generation module suggests the first column; if the Noon time range then on the $5^{th}$ column (i.e., the $1^{st}$ sub-column of column 2208); if the Evening time range then on the $9^{th}$ column (i.e., the $1^{st}$ sub-column of column 2210); and if for the Bed time range then on the $13^{th}$ column (i.e., the $1^{st}$ sub-column of column 2212). At that time, the plan generation module can generate the CFI, HOA, column number, and quantity for the slot for each prescription. This template filling process is performed for all prescriptions that are to be filled. Once the list is exhausted, then plan generation module can save the template to a database.

If the template already exists (i.e., for this patient and/or packing type), then the plan generation module loops through the rows of prescriptions. If the prescription is marked for filling, then the plan generation module retrieves template detail data and populates the quantity to be filled on the corresponding column number (in a similar manner to described above). If the drug (indicated by the template) is new and not in the template, the plan generation module automatically suggests the appropriate time slot, based on the logic above. Once all the HOA and column numbers are populated for a particular prescription/drug, the plan generation module processes the next prescription to be filled.

As shown by FIG. 22B, some of these HOAs are modified, such as by using method 2100. FIG. 22B illustrates a visualization 2250 of a template that is modified using the plan generation module, such as illustrated by FIG. 21. Template visualization 2250 includes several columns 2256-2262 which correspond to HOAs (analogous to HOAs 2206-2212 of FIG. 22A). Thus, there are four HOAs, morning 2256, afternoon 2258, evening 2260, and bedtime 2262. Template visualization 2250 includes several rows, each corresponding to a separate prescription. Furthermore, each HOA row contains four entries (also referred to as sub-rows), each of which corresponds to a separate pill pack. Thus, all sub-rows marked with "1" correspond to a first pill pack, all sub-rows marked with "2" correspond to a second pill pack, etc.

In this example, as modified from template visualization 2200, template visualization 2250 includes a second prescription 2252 that now indicates a drug usage time of 1 pm for afternoon dose 2206. As shown in FIG. 22B, the pill distributions were re-allocated from a first sub-row to a second sub-row, thus indicating that these re-allocated pills will be distributed using a second pill pack.

As shown by FIG. 22B, the plan generation module modifies the initially suggested template of FIG. 22A by splitting the morning dose in two. There are two packs for this fill, one pack containing only the Morning and Noon doses (two columns each), while the other pack contains the Evening and Bed doses. It is noted that the plan generation module can ignore individual column numbers, and instead take into account the number of columns and the dose times. Once modified, the template is saved.

Once the template is selected/modified, the plan generation module can suggest the total quantity required for the prescription being processed (i.e., being filled), such as based on the days supply of the pack and the quantity per HOA. Once the fill transaction is created, the plan generation module can first determine the number of columns/dose times that entire fill would need for one week, and then determine the number of pill packs that would be needed for a 7 day supply pack (or for another time period, as desired).

For example, the plan generation module can generate pill packs for a patient for a 14 day supply. If a fill for a seven-day supply has 6 columns/dose times, then one week's supply is broken into two seven day supply of bubble packs, as each bubble pack can have a maximum of four columns/dose times. Since the plan generation module is filling a 14 day supply, then the plan generation module can generate a plan that indicates using four packs for this patient. For each fill, a corresponding template data is also saved for each fill ID to aid in the data generation for robot filling.

In one embodiment, once the template is finalized, the plan generation module finalizes the fill data for each drug and HOA per day information that is used by the robot for performing the actual filling. It is noted that this can be also performed by the robot's control module instead. The plan generation module can retrieve the fill data for the fill transaction to obtain the number of columns/dose times. The plan generation module then loops through all the Rx's/drugs to plot the slots (of the pill pack to be filled). The plotting can use the current robot configuration and the type of pill packs being used. Using the known start of administration date (such as saved in the fill transaction) and the number of pills per HOA, the plan generation module can plot the particular slot on the pill pack for that HOA and day based on a pre-defined slot master. The master list can indicate on which slot the fill will go (e.g., slots 1 to 28 for a seven-day pill pack plotted by day Sunday, Monday, etc., against column/dose time).

As the plan generation module loops through, the plan generation module can increment the fill date (beginning with administration start date) by one (or alternatively, by another quantity) in order to get the day name to match in the slot master together with the column/dose time. After creating the plotted location, the plan generation module reduces the total fill quantity by the quantity of each HOA. If the number of columns and/or dose times exceeds four (or another number of sub-columns), then the plan generation module can create another set of data for another pill pack for this drug. Once the total quantity reaches zero, the plan generation module moves on to the next prescription/drug. In other words, during the plotting process, the plan generation module maps the template to a plan that is used by the robot to fill the physical pill pack(s) based on that template.

FIG. 23 is a block diagram of an example pill pack 2300, according to one embodiment. Pill pack 2300 includes a plurality of slots, one for each pill distribution. As shown, pill pack 2300 includes columns of pill distributions 2302(1)-2302(4), each column corresponding to a different time of day. Pill pack 2300 also includes rows of pill distributions 2304(1)-2304(7), each row corresponding to a different day of the week. As shown, both pill distributions 2302(3) and 2304(4) indicate that the pills contained in their respective slots correspond to the same bedtime HOA. In other words, the plan generation module can move the distribution of pills from the fourth HOA into the third HOA, as long as there are no pills to be distributed in that third HOA. After this re-allocation, the pill pack does not include any pills to be distributed in the afternoon HOA (the previous third HOA).

Furthermore, any changes to the pill distributions are also reflected by the labels that are applied to the pill pack. These label changes are a part of the pack data (as generated by the plan generation module). It is noted that the label changes are important, as the patient needs to know that, in the evening, s/he is will not take any pills; and instead, will take a larger amount of pills at nighttime. In the pill pack of FIG. 23, the label for the evening HOA is replaced by the bedtime HOA.

Example Computer Implementation

Figure 24:
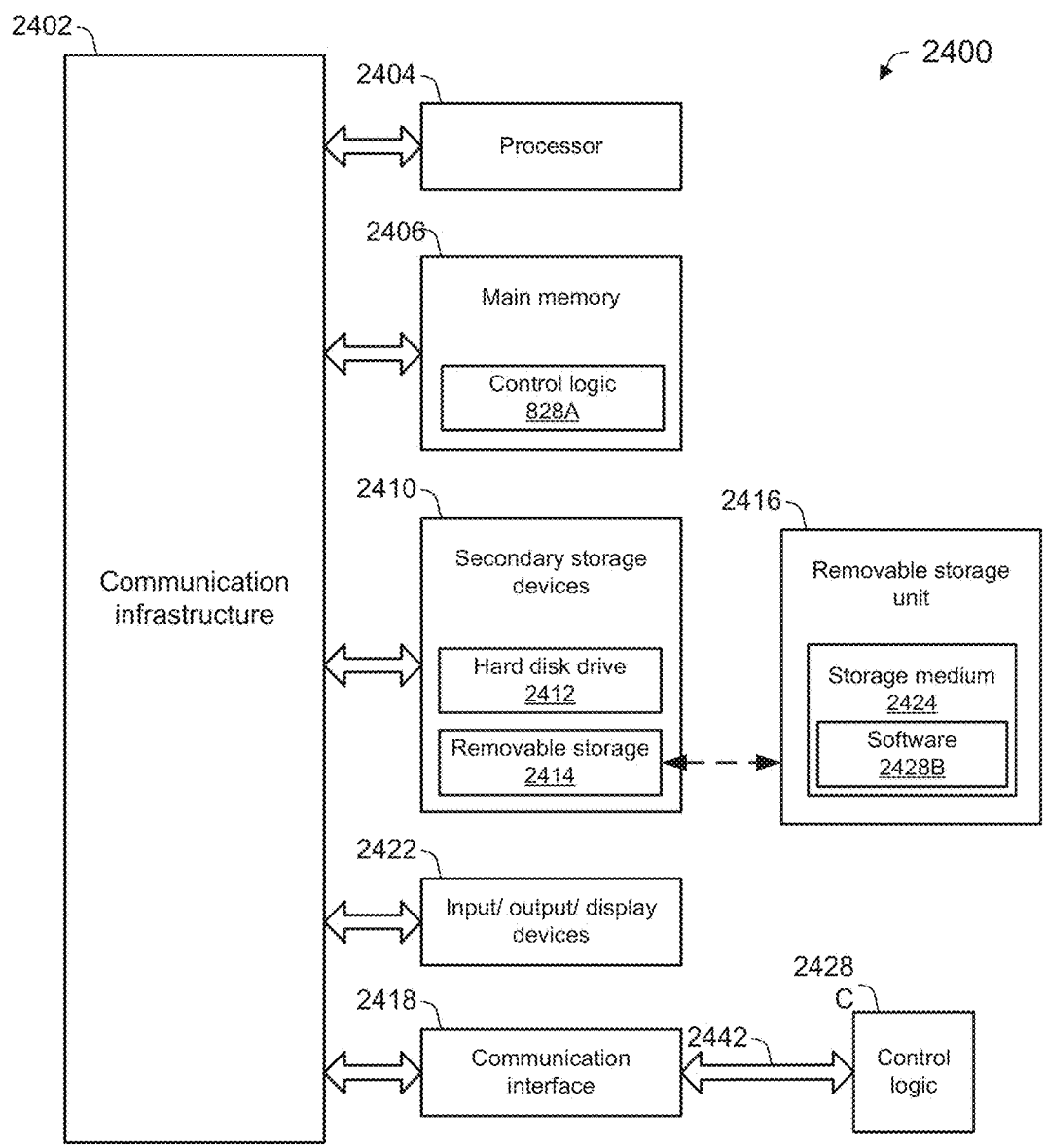
FIG. 24 is a block diagram of a computer system that can implement the control module of the pill dispensing robot, according to some embodiments.

The embodiments described herein, including systems, methods/processes, and/or apparatuses, may be implemented using well known servers/computers, such as computer 2400 shown in FIG. 24. For instance, elements of example pill dispensing robot 100, including any of computing devices 122, node 1500, any elements thereof, each of the steps of flowcharts 150, 600, 1300, 1400, 1600-2100, and the functionality depicted by FIGS. 7-12, can each be implemented using one or more computers 2400.

Computer 2400 can be any commercially available and well known computer capable of performing the functions described herein, such as computers available from International Business Machines, Apple, Sun, HP, Dell, Cray, etc. Computer 2400 may be any type of computer, including a desktop computer, a server, tablet PC, or mobile communication device, etc.

As shown in FIG. 24, computer 2400 includes one or more processors (e.g., central processing units (CPUs)), such as processor 2406. Processor 2406 may include any modules and/or layers of FIGS. 1, 7-12, and 15, and/or any portion or combination thereof, for example, though the scope of the embodiments is not limited in this respect. Processor 2406 is connected to a communication infrastructure 2402, such as a communication bus. In some embodiments, processor 2406 can simultaneously operate multiple computing threads.

Computer 2400 also includes a primary or main memory 2408, such as a random access memory (RAM). Main memory has stored therein control logic 2424A (computer software), and data.

Computer 2400 also includes one or more secondary storage devices 2410. Secondary storage devices 2410 include, for example, a hard disk drive 2412 and/or a removable storage device or drive 2414, as well as other types of storage devices, such as memory cards and memory sticks. For instance, computer 2400 may include an industry standard interface, such as a universal serial bus (USB) interface for interfacing with devices such as a memory stick. Removable storage drive 2414 represents a floppy disk drive, a magnetic tape drive, a compact disk drive, an optical storage device, tape backup, etc.

Removable storage drive 2414 interacts with a removable storage unit 2416. Removable storage unit 2416 includes a computer useable or readable storage medium 2418 having stored therein computer software 2424B (control logic) and/or data. Removable storage unit 2416 represents a floppy disk, magnetic tape, compact disc (CD), digital versatile disc (DVD), Blue-ray disc, optical storage disk, memory stick, memory card, or any other computer data storage device. Removable storage drive 2414 reads from and/or writes to removable storage unit 2416 in a well known manner.

Computer 2400 also includes input/output/display devices 2404, such as monitors, keyboards, pointing devices, etc. Computer 2400 further includes a communication or network interface 2420. Communication interface 2420 enables computer 2400 to communicate with mobile devices. For example, communication interface 2420 allows computer 2400 to communicate over communication networks or mediums 2422 (representing a form of a computer useable or readable medium), such as local area networks (LANs), wide area networks (WANs), the Internet, etc. Network interface 2420 may interface with remote sites or networks by using wired or wireless connections. Examples of communication interface 2422 include but are not limited to a modem, a network interface card (e.g., an Ethernet card), a communication port, a Personal Computer Memory Card International Association (PCMCIA) card, etc.

Control logic 2424C may be transmitted to and from computer 2400 by using the communication medium 2422. Any apparatus or manufacture comprising a computer useable or readable medium having control logic (software) stored therein is referred to herein as a computer program product or program storage device. This includes, but is not limited to, computer 2400, main memory 2408, secondary storage devices 2410, and removable storage unit 2416. Such computer program products, having control logic stored therein that, when executed by one or more data processing devices, because such data processing devices to operate as described herein, represent embodiments of the invention.

For example, each of the elements of the computing device 122, node 1500, control module 128 and/or plan generation module 124 depicted in FIGS. 1, 7-12, and 15 can be implemented as control logic that may be stored on a computer useable medium or computer readable medium, which can be executed by one or more processors to operate as described herein.

Data Structures

In some embodiments, the following data structures, such as templates, are used by the plan generation module when generating pack data. However, different, additional, and/or fewer data structures can be used instead, as desired. In another embodiment, data objects can be used instead, which may have similar members as what is discussed below.

TEMPLATE PER PATIENT AND PACKING TYPE— this template information is pulled for each fill

| fill_pack_column_setup_header | | |
|---|---|---|
| tran_id | unique ID | |
| patient_id | patient ID | |
| packing_id | pack ID | different packs might have different fill days |

| fill_pack_column_setup_detail | |
|---|---|
| tran_id | unique ID |
| Txr | CFI (Clinical Formulation ID) |
| hoa | Hours of Administration |
| pack_column_no | Pack column number, range is 1 to 16 which will help determine the location of the slot |
| qty_per_slot | Quantity per slot/column |

| TEMPLATE PER SPECIFIC PACK FILLED - this information helps translating for sending the data to the robot for filling | |
|---|---|
| tran_id | unique ID     same as filled pack ID |
| sr_id | series ID |
| rx_id | Prescription tran_id or primary key |
| hoa | Hours of Administration |
| pack_column_no | Pack column number, range is 1 to 16 which will help determine the location of the slot |
| hoa_qty | quantity per hoa of administration/slot |

The following are data structures, such as templates, that are used by the control module when operating the robot. However, different, additional, and/or fewer data structures can be used instead, as desired. In another embodiment, data objects can be used instead, which may have similar members as what is discussed below.

The following are examples of plan/pack data being sent from the IPS (i.e., the plan generation module).

| r_batch_packs_dtl | |
|---|---|
| tran_id | Unique ID |
| batch_id | filled pack ID |
| patient_id | Patient ID ( From patient_master table ) |
| date_from | Fill start date |
| date_to Fill | upto date |
| sr_id Series | ID |
| hoa | Hours of administration |
| mneb | Morning/Noon/Evening/Bedtime |
| drug_size | Size of the drug |
| drug_id | Drug ID ( From drug_master table) |
| fill_qty | Fill qty |
| colname x | position in the pack |
| day_number y | position in the pack |

| r_batch_slot_details | |
|---|---|
| tran_id | Unique ID |
| batch_id | filled pack ID |
| patient_id | Patient ID ( From patient_master table ) |
| date_from | Specific Fill date |
| pack_no | Pack number |
| slot_no Pack | slot number |
| drug_id | Drug ID ( From drug_master table ) |
| canister_id | Canister ID ( From canister_master table ) |
| fill_qty | Qty to drop |
| filled | Filled flag |
| filled_by | User who filled the pack |
| tray_no | Tray number |
| tray_slot_no | Tray slot number |
| filled_qty | Total qty filled |
| queue_id | Queue ID ( From r_robot_queue ) |
| hoa | Hours of administration |
| robot_id | Robot ID |

The following are examples of pack data in Queue(s), such as used for label printing and filling.

| r_robot_queue | |
|---|---|
| queue_id | Queue ID |
| queue_datetime | Queued date and time |
| queue_status | Queue Status |

TABLE-continued

| r_robot_queue | |
| --- | --- |
| queued_by | User who queued the pack(s) |
| changed_date | Status changed date and time |

TABLE

| r_robot_queue_dtl | |
| --- | --- |
| queue_id | Queue ID from Queue ID |
| sr_id | Series ID |
| batch_id filled | pack ID |
| patient_id | Patient ID ( From patient_master table ) |
| pack_no | Pack number |
| status | Pack status |
| last_filled_by | User who filled |

The following are examples of data used by the canister master (i.e., a control module (or a portion of the robot's control module) that is operating the canister module).

TABLE

| r_canister_master | |
| --- | --- |
| canister_id | Canister ID |
| drug_id | Drug ID ( from drug_master table ) |
| rf_id | RF ID |
| available_qty | Canister drug qty |
| reorder_qty | Reorder level qty |
| in_queue_qty | Qty in queue |
| boxnumber | Canister location in the robot |
| active | Active flag |
| robot_id | Robot ID |

The following are examples of data used by the canister master (i.e., a control module (or a portion of the robot's control module) that is operating the canister module) for canister fill and/or adjustment history.

TABLE

| r_canister_adj | |
| --- | --- |
| tran_id | Unique ID |
| canister_id | Canister ID ( from canister master table ) |
| rf_id | RFID |
| drug_id | Drug ID |
| adj_datetime | Date and time |
| adj_by | User ID |
| adj_qty | Fill/Adjustment qty |
| lot_no | Lot number |
| exp_date | Expiration date |
| adj_type | Fill or Adjustment |
| slot_tran_id | Slot tran id |
| fillq_tran_id | Fill queue |

Although the present invention has been described in connection with several embodiments, the invention is not intended to be limited to the specific forms set forth herein. On the contrary, it is intended to cover such alternatives, modifications, and equivalents as can be reasonably included within the scope of the invention as defined by the appended claims.

What is claimed is:

1. A method comprising:
    accessing a plan, wherein
        the plan indicates
            a first pill distribution for a first period of time, and
            a second pill distribution for a second period of time;
    receiving an input, wherein
        the input indicates a desired change to the plan,
        the input indicates at least one pill to be distributed in the first period of time;
    determining whether to modify one or more of the first pill distribution or the second pill distribution; and
    in response to a determination that the second pill distribution is to be modified,
        modifying the plan to indicate a change in the second pill distribution and reconfiguring a pill packaging (pill pack) in which the first and second pills are to be distributed, wherein the reconfigured pill pack reflects the pill distribution according to the modified plan, wherein the modified plan includes relabeling of columns in the pill pack such that pills with the same hours of administration are merged such that two columns with two separate hours of administration are relabeled so that the two columns share a same designation.

2. The method of claim 1, wherein
    each of the first pill distribution and the second pill distribution indicate distributions of pills in a pill pack,
    the pill pack is configured to hold a plurality of pills,
    the plurality of pills are separated by a plurality of columns, and
    the each of the columns indicates a separate period of time.

3. The method of claim 1, wherein
    the plan is configured to be transmitted to a robot,
    the robot is configured to, in response to a receipt of the plan,
        select a first plurality of pills according to the plan, and
        dispense the first plurality of pills into a pill pack, according to the plan.

4. The method of claim 1, wherein
    the determining whether to modify one or more of the first pill distribution or the second pill distribution is based on one or more of
        a current capacity of each of elements in the pill pack for the first pill distribution, or
        a projected capacity of each of elements in the pill pack for the second pill distribution.

5. The method of claim 1, wherein
    the determining comprises one or more of:
        determining whether to use two or more pill packs for the first pill distribution and the second pill distribution, or
        determining whether to use two or more columns of a pill pack for one or more of
            the first pill distribution, or
            the second pill distribution.

6. The method of claim 5,
    the determination that the second pill distribution is to be modified comprises a determination whether to use the two or more columns of the pill pack for the first pill distribution.

7. The method of claim 1, wherein
    after the modifying, the second pill distribution indicates pills to be distributed in the first period of time.

8. The method of claim 1, further comprising:
    generating label changes for the pill pack to indicate the change in the second pill distribution.

9. A system comprising:
    one or more processors; and
    a plan generation module, executable by the one or more processors, and configured to:

access a plan, wherein
  the plan indicates
    a first pill distribution for a first period of time, and
    a second pill distribution for a second period of time, receive an input, wherein
  the input indicates a change to the plan,
  the input indicates at least one pill to be distributed in the first period of time,
determine whether to modify one or more of the first pill distribution or the second pill distribution, and
in response to a determination that the second pill distribution is to be modified,
  modify the plan to indicate changes in the second pill distribution and reconfiguring a pill packaging (pill pack) in which the first and second pills are to be distributed, wherein the reconfigured pill pack reflects the pill distribution according to the modified plan, wherein the modified plan includes relabeling of columns in the pill pack such that pills with the same hours of administration are merged such that two columns with two separate hours of administration are relabeled so that the two columns share a same designation.

10. The system of claim 9, wherein
each of the first pill distribution and the second pill distribution indicate distributions of pills in a pill pack,
the pill pack is configured to hold a plurality of pills,
the plurality of pills are separated by a plurality of columns, and
the each of the columns indicates a separate period of time.

11. The system of claim 9, wherein
the plan is configured to be transmitted to a robot,
the robot is configured to, in response to a receipt of the plan,
  select a first plurality of pills according to the plan, and
  dispense the first plurality of pills into a pill pack, according to the plan.

12. The system of claim 9, wherein
the plan generation module is configured to perform the determination based on one or more of
  a current capacity of each of elements in the pill pack for the first pill distribution, or
  a projected capacity of each of elements in the pill pack for the second pill distribution.

13. The system of claim 9, wherein
the plan generation module is configured to perform the determination based on one or more of
  determining whether to use two or more pill packs for the first pill distribution and the second pill distribution, or
  determining whether to use two or more columns of a pill pack for one or more of
    the first pill distribution, or
    the second pill distribution.

14. The system of claim 9, wherein
the plan generation module is configured to perform the determination comprises a determination whether to use the two or more columns of the pill pack for the first pill distribution.

15. The system of claim 9, wherein
after the plan generation module performs the modification, the second pill distribution indicates pills to be distributed in the first period of time.

16. The system of claim 9, wherein
the plan generation module is further configured to indicate one or more label changes for the pill pack for indicating the change in the second pill distribution.

17. A computer program product comprising:
a plurality of instructions, comprising
  a first set of instructions, executable on a computer system, configured to access a plan, wherein
    the plan indicates
      a first pill distribution for a first period of time, and
      a second pill distribution for a second period of time,
  a second set of instructions, executable on a computer system, configured to receive an input, wherein
    the input indicates a change to the plan,
    the input indicates at least one pill to be distributed in the first period of time,
  a third set of instructions, executable on a computer system, configured to determine whether to modify one or more of the first pill distribution or the second pill distribution, and
  a fourth set of instructions, executable on a computer system, configured to,
    in response to a determination that the second pill distribution is to be modified, modify the plan to indicate changes in the second pill distribution and reconfiguring a pill packaging (pill pack) in which the first and second pills are to be distributed, wherein the reconfigured pill pack reflects the pill distribution according to the modified plan, wherein the modified plan includes relabeling of columns in the pill pack such that pills with the same hours of administration are merged such that two columns with two separate hours of administration are relabeled so that the two columns share a same designation; and
wherein the plurality of instructions are configured to be executed using one or more processors.

18. The computer program product of claim 17, wherein
the third set of instructions is further configured to perform the determination based on one or more of
  a current capacity of each of elements in the pill pack for the first pill distribution, or
  a projected capacity of each of elements in the pill pack for the second pill distribution.

19. The computer program product of claim 17, wherein,
the third set of instructions is further configured to perform the determination comprising one or more of
  determining whether to use two or more pill packs for the first pill distribution and the second pill distribution, or
  determining whether to use two or more columns of a pill pack for one or more of
    the first pill distribution, or
    the second pill distribution.

20. The computer program product of claim 17, wherein
after a modification of the plan, the second pill distribution indicates pills that are to be distributed in the first period of time.

* * * * *